United States Patent
Solem

(10) Patent No.: US 9,295,484 B2
(45) Date of Patent: Mar. 29, 2016

(54) DEVICE, A KIT AND A METHOD FOR TREATMENT OF DISORDERS IN THE HEART RHYTHM REGULATION SYSTEM

(75) Inventor: Jan Otto Solem, Stetten (CH)

(73) Assignee: Syntach AG, Schaffhausen (CH)

( * ) Notice: Subject to any disclaimer, the term of this patent is extended or adjusted under 35 U.S.C. 154(b) by 1250 days.

(21) Appl. No.: 12/486,678

(22) Filed: Jun. 17, 2009

(65) Prior Publication Data
US 2009/0264983 A1 Oct. 22, 2009

Related U.S. Application Data

(62) Division of application No. 10/989,551, filed on Nov. 17, 2004, now abandoned.

(30) Foreign Application Priority Data

Nov. 17, 2003 (SE) .................................. 0303017

(51) Int. Cl.
| | |
|---|---|
| *A61B 17/32* | (2006.01) |
| *A61B 17/3205* | (2006.01) |
| *A61B 17/00* | (2006.01) |
| *A61B 18/00* | (2006.01) |

(Continued)

(52) U.S. Cl.
CPC .............. *A61B 17/32* (2013.01); *A61B 17/3205* (2013.01); *A61B 17/320016* (2013.01); *A61B 2017/00243* (2013.01); *A61B 2017/00247* (2013.01); *A61B 2017/00292* (2013.01); *A61B 2017/00867* (2013.01); *A61B 2018/00392* (2013.01); *A61F 2/2493* (2013.01); *A61F 2/91* (2013.01); *A61F 2002/249* (2013.01)

(58) Field of Classification Search
CPC ................... A61B 17/320016; A61B 17/3205; A61B 2017/00243; A61B 2017/00247; A61B 2017/00292; A61B 2017/00867; A61F 2/2493; A61F 2/91; A61F 2002/249
USPC .......... 623/1.14, 1.18, 1.2; 606/167, 179, 180, 606/159
See application file for complete search history.

(56) References Cited

U.S. PATENT DOCUMENTS

| 4,016,886 A | 4/1977 | Doss et al. |
| 4,296,100 A | 10/1981 | Franco |

(Continued)

FOREIGN PATENT DOCUMENTS

| EP | 0 227 230 A1 | 7/1987 |
| EP | 0 467 516 A1 | 1/1992 |

(Continued)

OTHER PUBLICATIONS http://www.thefreedictionary.com/laceration, definition of the term laceration retrieved on Jun. 19, 2012.*

(Continued)

*Primary Examiner* — David C Eastwood
(74) *Attorney, Agent, or Firm* — Inskeep IP Group, Inc.

(57) ABSTRACT

A tissue lesion creating device is structured and arranged to be inserted through the vascular system into a body vessel adjacent the heart and to be subsequently subjected to a change of shape in order to penetrate into the heart tissue. The tissue lesion creating device may thus be used for treating disorders to the heart rhythm regulation system. A kit of devices provides a plurality of devices for creating a lesion pattern for treating such disorders.

20 Claims, 24 Drawing Sheets

(51) Int. Cl.
*A61F 2/24* (2006.01)
*A61F 2/91* (2013.01)

(56) References Cited

U.S. PATENT DOCUMENTS

| | | | |
|---|---|---|---|
| 4,580,568 A | 4/1986 | Gianturco | |
| 4,638,803 A | 1/1987 | Rand | |
| 4,791,928 A | 12/1988 | Berke et al. | |
| 4,844,099 A | 7/1989 | Skalsky et al. | |
| 4,886,074 A | 12/1989 | Bisping | |
| 4,953,564 A | 9/1990 | Berthelsen | |
| 5,002,067 A | 3/1991 | Berthelsen et al. | |
| 5,019,396 A | 5/1991 | Ayer et al. | |
| 5,152,299 A | 10/1992 | Soukup | |
| 5,167,614 A * | 12/1992 | Tessmann et al. | 623/1.15 |
| 5,176,135 A | 1/1993 | Fain et al. | |
| 5,234,448 A | 8/1993 | Wholey et al. | |
| 5,239,999 A | 8/1993 | Imran | |
| 5,244,460 A | 9/1993 | Unger et al. | |
| 5,246,438 A | 9/1993 | Langberg | |
| 5,254,127 A | 10/1993 | Wholey et al. | |
| 5,281,213 A | 1/1994 | Milder et al. | |
| 5,281,218 A | 1/1994 | Imran | |
| 5,282,844 A | 2/1994 | Stokes et al. | |
| 5,295,484 A | 3/1994 | Marcus et al. | |
| 5,312,456 A | 5/1994 | Reed et al. | |
| 5,324,324 A | 6/1994 | Vachon et al. | |
| 5,342,414 A | 8/1994 | Mehra | |
| 5,360,440 A | 11/1994 | Andersen | |
| 5,370,675 A | 12/1994 | Edwards et al. | |
| 5,387,007 A | 2/1995 | Ogawa et al. | |
| 5,387,419 A | 2/1995 | Levy et al. | |
| 5,403,311 A | 4/1995 | Abele et al. | |
| 5,405,376 A | 4/1995 | Mulier et al. | |
| 5,411,535 A | 5/1995 | Fujii et al. | |
| 5,423,851 A | 6/1995 | Samuels | |
| 5,431,649 A | 7/1995 | Mulier et al. | |
| 5,466,255 A | 11/1995 | Franchi | |
| 5,507,779 A | 4/1996 | Altman | |
| 5,509,924 A | 4/1996 | Paspa et al. | |
| 5,527,344 A | 6/1996 | Arzbaecher et al. | |
| 5,531,779 A | 7/1996 | Dahl et al. | |
| 5,545,183 A | 8/1996 | Altman | |
| 5,551,426 A | 9/1996 | Hummel et al. | |
| 5,551,427 A | 9/1996 | Altman | |
| 5,569,272 A | 10/1996 | Reed et al. | |
| 5,580,569 A | 12/1996 | Giampapa | |
| 5,584,879 A | 12/1996 | Reimold et al. | |
| 5,609,628 A | 3/1997 | Keranen | |
| 5,618,310 A | 4/1997 | Ger et al. | |
| 5,622,698 A | 4/1997 | Lee, Jr. | |
| 5,634,936 A | 6/1997 | Linden et al. | |
| 5,649,906 A | 7/1997 | Gory et al. | |
| 5,658,327 A | 8/1997 | Altman et al. | |
| 5,662,698 A | 9/1997 | Altman et al. | |
| 5,674,272 A | 10/1997 | Bush et al. | |
| 5,676,850 A | 10/1997 | Reed et al. | |
| 5,697,909 A | 12/1997 | Eggers et al. | |
| 5,707,385 A | 1/1998 | Williams | |
| 5,713,863 A | 2/1998 | Vigil et al. | |
| 5,725,567 A | 3/1998 | Wolff et al. | |
| 5,749,890 A | 5/1998 | Shaknovich | |
| 5,749,922 A | 5/1998 | Slepian et al. | |
| 5,769,883 A | 6/1998 | Buscemi et al. | |
| 5,824,030 A | 10/1998 | Yang et al. | |
| 5,833,715 A | 11/1998 | Vachon et al. | |
| 5,837,007 A | 11/1998 | Altman et al. | |
| 5,843,169 A | 12/1998 | Taheri | |
| 5,879,349 A | 3/1999 | Edwards | |
| 5,891,108 A | 4/1999 | Leone et al. | |
| 5,899,917 A | 5/1999 | Edwards et al. | |
| 5,904,713 A | 5/1999 | Leschinsky | |
| 5,910,144 A | 6/1999 | Hayashi | |
| 5,921,982 A | 7/1999 | Lesh et al. | |
| 5,928,181 A | 7/1999 | Coleman et al. | |
| 5,938,659 A | 8/1999 | Tu et al. | |
| 5,938,660 A | 8/1999 | Swartz et al. | |
| 5,941,845 A | 8/1999 | Tu et al. | |
| 5,944,715 A | 8/1999 | Goble et al. | |
| 5,954,761 A | 9/1999 | Machek et al. | |
| 5,964,756 A | 10/1999 | McGaffigan et al. | |
| 5,971,983 A | 10/1999 | Lesh | |
| 5,980,519 A | 11/1999 | Hahnen et al. | |
| 6,002,955 A | 12/1999 | Willems et al. | |
| 6,009,877 A | 1/2000 | Edwards | |
| 6,010,531 A | 1/2000 | Donlon et al. | |
| 6,012,457 A | 1/2000 | Lesh | |
| 6,023,638 A | 2/2000 | Swanson | |
| 6,024,740 A | 2/2000 | Lesh et al. | |
| 6,030,384 A | 2/2000 | Nezhat | |
| 6,086,582 A | 7/2000 | Altman et al. | |
| 6,086,586 A | 7/2000 | Hooven | |
| 6,102,887 A | 8/2000 | Altman | |
| 6,106,524 A | 8/2000 | Eggers et al. | |
| 6,117,101 A | 9/2000 | Diedrich et al. | |
| 6,152,144 A * | 11/2000 | Lesh et al. | 128/898 |
| 6,152,920 A | 11/2000 | Thompson et al. | |
| 6,161,029 A | 12/2000 | Spreigl et al. | |
| 6,161,543 A | 12/2000 | Cox et al. | |
| 6,164,283 A | 12/2000 | Lesh | |
| 6,179,858 B1 | 1/2001 | Squire et al. | |
| 6,206,914 B1 | 3/2001 | Soykan et al. | |
| 6,210,392 B1 | 4/2001 | Vigil et al. | |
| 6,224,491 B1 | 5/2001 | Hiromi et al. | |
| 6,224,626 B1 | 5/2001 | Steinke | |
| 6,231,570 B1 | 5/2001 | Tu et al. | |
| 6,236,891 B1 | 5/2001 | Ingle et al. | |
| 6,241,726 B1 | 6/2001 | Raymond Chia et al. | |
| 6,254,632 B1 | 7/2001 | Wu et al. | |
| 6,267,776 B1 | 7/2001 | O'Connell | |
| 6,270,476 B1 | 8/2001 | Santoianni et al. | |
| 6,283,992 B1 | 9/2001 | Hankh et al. | |
| 6,293,964 B1 | 9/2001 | Yadav | |
| 6,296,630 B1 | 10/2001 | Altman et al. | |
| 6,305,378 B1 | 10/2001 | Lesh | |
| 6,315,778 B1 | 11/2001 | Gambale et al. | |
| RE37,463 E | 12/2001 | Altman | |
| 6,325,797 B1 | 12/2001 | Stewart et al. | |
| 6,346,099 B1 | 2/2002 | Altman | |
| 6,358,247 B1 | 3/2002 | Altman et al. | |
| 6,375,666 B1 * | 4/2002 | Mische | 606/198 |
| 6,395,026 B1 | 5/2002 | Aboul-Hosn et al. | |
| 6,405,732 B1 | 6/2002 | Edwards et al. | |
| 6,425,895 B1 | 7/2002 | Swanson et al. | |
| 6,438,427 B1 | 8/2002 | Rexhausen et al. | |
| 6,443,949 B2 | 9/2002 | Altman | |
| 6,464,697 B1 | 10/2002 | Edwards et al. | |
| 6,500,186 B2 | 12/2002 | Lafontaine et al. | |
| 6,503,247 B2 | 1/2003 | Swartz et al. | |
| 6,508,834 B1 | 1/2003 | Pinshasik et al. | |
| 6,514,249 B1 | 2/2003 | Maguire et al. | |
| 6,529,756 B1 | 3/2003 | Phan et al. | |
| 6,547,788 B1 | 4/2003 | Maguire et al. | |
| 6,558,382 B2 | 5/2003 | Jahns et al. | |
| 6,572,652 B2 | 6/2003 | Shaknovich | |
| 6,577,895 B1 | 6/2003 | Altman | |
| 6,622,731 B2 | 9/2003 | Daniel et al. | |
| 6,625,486 B2 | 9/2003 | Lundkvist et al. | |
| 6,632,223 B1 | 10/2003 | Keane | |
| 6,640,120 B1 | 10/2003 | Swanson et al. | |
| 6,702,844 B1 | 3/2004 | Lazarus | |
| 6,702,850 B1 | 3/2004 | Byun et al. | |
| 6,723,092 B2 | 4/2004 | Brown et al. | |
| 6,746,460 B2 | 6/2004 | Gannoe et al. | |
| 6,837,886 B2 | 1/2005 | Collins et al. | |
| 6,893,438 B2 | 5/2005 | Hall et al. | |
| 6,904,303 B2 | 6/2005 | Phan et al. | |
| 6,953,560 B1 | 10/2005 | Castro et al. | |
| 6,962,587 B2 | 11/2005 | Johnson et al. | |
| 7,008,418 B2 | 3/2006 | Hall et al. | |
| 7,077,860 B2 | 7/2006 | Yan et al. | |
| 7,182,771 B1 | 2/2007 | Houser et al. | |
| 7,198,675 B2 | 4/2007 | Fox et al. | |
| 7,285,119 B2 | 10/2007 | Stewart et al. | |

(56) References Cited

U.S. PATENT DOCUMENTS

| | | |
|---|---|---|
| 7,410,486 B2 | 8/2008 | Fuimaono et al. |
| 7,731,747 B2 | 6/2010 | Kaplan et al. |
| 2001/0001317 A1 | 5/2001 | Duerig et al. |
| 2001/0004683 A1 | 6/2001 | Gambale et al. |
| 2001/0004690 A1 | 6/2001 | Gambale et al. |
| 2001/0004705 A1 | 6/2001 | Killion et al. |
| 2001/0007070 A1 | 7/2001 | Stewart et al. |
| 2001/0018611 A1* | 8/2001 | Solem et al. ............... 623/2.37 |
| 2001/0027340 A1 | 10/2001 | Wright et al. |
| 2001/0029366 A1* | 10/2001 | Swanson et al. ............... 606/29 |
| 2001/0032014 A1 | 10/2001 | Yang et al. |
| 2001/0044619 A1 | 11/2001 | Altman |
| 2002/0002401 A1 | 1/2002 | McGuckin, Jr. et al. |
| 2002/0010462 A1 | 1/2002 | Altman |
| 2002/0012060 A1 | 1/2002 | High et al. |
| 2002/0013275 A1 | 1/2002 | Kunz et al. |
| 2002/0019623 A1 | 2/2002 | Altman et al. |
| 2002/0026228 A1 | 2/2002 | Schauerte |
| 2002/0026233 A1 | 2/2002 | Shaknovich |
| 2002/0077691 A1 | 6/2002 | Nachtigall |
| 2002/0091433 A1 | 7/2002 | Ding et al. |
| 2002/0115990 A1 | 8/2002 | Acker |
| 2002/0120260 A1 | 8/2002 | Morris et al. |
| 2002/0120263 A1 | 8/2002 | Brown et al. |
| 2002/0142119 A1 | 10/2002 | Seward et al. |
| 2002/0151918 A1 | 10/2002 | Lafontaine et al. |
| 2002/0161377 A1 | 10/2002 | Rabkin |
| 2002/0165532 A1 | 11/2002 | Hill, III et al. |
| 2002/0169498 A1* | 11/2002 | Kim et al. ............... 623/1.15 |
| 2002/0183738 A1 | 12/2002 | Chee et al. |
| 2002/0188170 A1 | 12/2002 | Santamore et al. |
| 2003/0018362 A1 | 1/2003 | Fellows et al. |
| 2003/0040791 A1 | 2/2003 | Oktay |
| 2003/0055491 A1* | 3/2003 | Schwartz et al. ............... 623/1.21 |
| 2003/0065240 A1 | 4/2003 | Sanders et al. |
| 2003/0065307 A1* | 4/2003 | Lesh ............... 604/509 |
| 2003/0069606 A1 | 4/2003 | Girouard et al. |
| 2003/0069636 A1 | 4/2003 | Solem et al. |
| 2003/0074049 A1 | 4/2003 | Hoganson et al. |
| 2003/0078649 A1 | 4/2003 | Camrud et al. |
| 2003/0104347 A1 | 6/2003 | Mori et al. |
| 2003/0135267 A1 | 7/2003 | Solem et al. |
| 2003/0144658 A1 | 7/2003 | Schwartz et al. |
| 2003/0153971 A1 | 8/2003 | Chandrasekaran |
| 2003/0204240 A1 | 10/2003 | Letort |
| 2003/0216770 A1 | 11/2003 | Persidsky et al. |
| 2004/0106952 A1 | 6/2004 | Lafontaine |
| 2004/0116965 A1 | 6/2004 | Falkenberg |
| 2004/0158313 A1 | 8/2004 | Altman |
| 2004/0167598 A1* | 8/2004 | Margolis ............... 623/1.11 |
| 2004/0193247 A1 | 9/2004 | Besselink |
| 2004/0215310 A1 | 10/2004 | Amirana |
| 2004/0220655 A1 | 11/2004 | Swanson et al. |
| 2004/0243107 A1 | 12/2004 | Macoviak et al. |
| 2004/0249443 A1 | 12/2004 | Shanley et al. |
| 2004/0254597 A1* | 12/2004 | Schwartz et al. ............... 606/167 |
| 2004/0266716 A1 | 12/2004 | Donahue et al. |
| 2005/0014995 A1 | 1/2005 | Amundson et al. |
| 2005/0015129 A1 | 1/2005 | Mische |
| 2005/0143801 A1 | 6/2005 | Aboul-Hosn |
| 2005/0234540 A1 | 10/2005 | Peavey et al. |
| 2005/0288769 A1 | 12/2005 | Globerman |
| 2007/0110785 A1 | 5/2007 | Tedeschi |

FOREIGN PATENT DOCUMENTS

| | | |
|---|---|---|
| EP | 0 497 620 A2 | 8/1992 |
| EP | 0 558 352 A1 | 9/1993 |
| EP | 0 601 338 A1 | 6/1994 |
| EP | 1 290 987 A2 | 3/2003 |
| EP | 1 574 693 A1 | 9/2005 |
| WO | WO 94/07564 A2 | 4/1994 |
| WO | WO 99/52423 A1 | 10/1999 |
| WO | WO 99/55254 A1 | 11/1999 |
| WO | WO 00/12832 A2 | 3/2000 |
| WO | WO 00/16850 A1 | 3/2000 |
| WO | WO 00/36997 A1 | 6/2000 |
| WO | WO 00/42934 A1 | 7/2000 |
| WO | WO 00/64355 A1 | 11/2000 |
| WO | WO 00/67656 A1 | 11/2000 |
| WO | WO 01/19269 A1 | 3/2001 |
| WO | WO 01/26585 A1 | 4/2001 |
| WO | WO 01/26727 A1 | 4/2001 |
| WO | WO 01/64123 A2 | 9/2001 |
| WO | WO 02/00273 A2 | 1/2002 |
| WO | WO 02/24106 A2 | 3/2002 |
| WO | WO 02/058594 A1 | 8/2002 |
| WO | WO 02/071980 A2 | 9/2002 |
| WO | WO 03/003948 A1 | 1/2003 |
| WO | WO 2004/078065 A2 | 9/2004 |
| WO | WO 2005/048881 A1 | 6/2005 |
| WO | WO 2006/042246 A2 | 4/2006 |
| WO | WO 2006/122961 A1 | 11/2006 |
| WO | WO 2007/055397 A1 | 5/2007 |

OTHER PUBLICATIONS http://www.thefreedictionary.com/pierce, definition of the term pierce, retrieved Aug. 14, 2012.*

WIPO, International Search Report for International Application No. PCT/EP2004/012799 (International Filing Date Nov. 11, 2004), mailed Mar. 3, 2005, 7 pages.

*The Third Annual Conference on the Surgical Treatment of Atrial Fibrillation* (Jun. 18-19, 2003).

Damiano, Ralph J., Jr., M.D., "Alternative Energy Sources for Atrial Ablation: Judging the New Technology," *Ann. Thorac. Surg.* (2003) vol. 75, pp. 329-330.

Benussi, Stefano, M.D., Ph.D., et al., "A Tailored Anatomical Approach to Prevent Complications During Left Atrial Ablation," *Ann. Thorac. Surg.*, vol. 75 (2003) pp. 1979-1981.

Benussi, Stefano, M.D., Ph.D., et al., "Surgical Ablation of Atrial Fibrillation Using the Epicardial Radiofrequency Approach: Mid-Term Results and Risk Analysks," *Ann Thorac Surg*, 2002;74:1050-7.

Benussi, Stefano, M.D., Ph.D., et al., "A simple way to treat chronic atrial fibrillation during mitral valve surgery: the epicardial radiofrequency approach," *European Journal of Cardio-thoracic Surgery* (2000) vol. 17, pp. 524-529.

Cox, J.L., et al., "The surgical treatment of atrial fibrillation, II. Intraoperative electrophysiologic mapping and description of the electrophysiologic basis of atrial flutter and atrial fibrillation," *J. Thorac. Cardiovasc. Surg.* (1991) vol. 101, pp. 406-426.

Sandöe, E., et al., "Arrhythmia, Diagnosis and Management, A Clinical Electrocardiographic Guide," *Fachmed AG* (1984) pp. 2-11.

United States Patent and Trademark Office, Office Action mailed Feb. 2, 2011 in U.S. Appl. No. 12/298,452, 15 pages.

United States Patent and Trademark Office, Final Office Action mailed Jan. 25, 2011 in U.S. Appl. No. 12/396,329, 24 pages.

United States Patent and Trademark Office, Final Office Action mailed Nov. 19, 2011 in U.S. Appl. No. 11/910,607, 12 pages.

United States Patent and Trademark Office, Office Action mailed Oct. 7, 2010 in U.S. Appl. No. 11/333,966, 14 pages.

United States Patent and Trademark Office, Office Action mailed Oct. 1, 2010 in U.S. Appl. No. 12/486,690, 14 pages.

United States Patent and Trademark Office, Office Action mailed Sep. 30, 2010 in U.S. Appl. No. 12/486,678, 16 pages.

United States Patent and Trademark Office, Office Action mailed Sep. 16, 2010 in U.S. Appl. No. 10/989,551, 17 pages.

United States Patent and Trademark Office, Office Action mailed Sep. 16, 2010 in U.S. Appl. No. 11/910,736, 14 pages.

European Patent Office, Examination Report dated Sep. 15, 2010 in European Patent Application No. EP02 763 249.6-1257, 5 pages.

United States Patent and Trademark Office, Office Action mailed Jul. 9, 2010 in U.S. Appl. No. 11/246,412, 16 pages.

United States Patent and Trademark Office, Office Action mailed Jun. 3, 2010 in U.S. Appl. No. 11/551,670, 8 pages.

United States Patent and Trademark Office, Office Action mailed May 27, 2010 in U.S. Appl. No. 12/396,350, 10 pages.

United States Patent and Trademark Office, Office Action mailed

(56) References Cited

OTHER PUBLICATIONS

May 18, 2010 in U.S. Appl. No. 11/910,607, 14 pages.
United States Patent and Trademark Office, Office Action mailed May 14, 2010 in U.S. Appl. No. 12/396,298, 19 pages.
WIPO, European International Preliminary Examining Authority, International Search Report and Written Opinion mailed Apr. 16, 2010 in International Patent Application No. PCT/EP2007/061116, 13 pages.
United States Patent and Trademark Office, Final Office Action mailed Apr. 13, 2010 in U.S. Appl. No. 11/333,966, 14 pages.
United States Patent and Trademark Office, Final Office Action mailed Mar. 18, 2010 in U.S. Appl. No. 10/989,551, 12 pages.
United States Patent and Trademark Office, Office Action mailed Sep. 17, 2009 in U.S. Appl. No. 11/670,148, 11 pages.
United States Patent and Trademark Office, Office Action mailed Sep. 14, 2009 in U.S. Appl. No. 11/246,412, 23 pages.
United States Patent and Trademark Office, Office Action mailed Aug. 3, 2009 in U.S. Appl. No. 10/792,110, 6 pages.
United States Patent and Trademark Office, Office Action mailed Jul. 6, 2009 in U.S. Appl. No. 10/989,551, 20 pages.
United States Patent and Trademark Office, Office Action mailed May 14, 2009 in U.S. Appl. No. 11/457,756, 12 pages.
United States Patent and Trademark Office, Final Office Action mailed Mar. 11, 2009 in U.S. Appl. No. 11/337,618, 11 pages.
WIPO, U.S. International Preliminary Examining Authority, International Preliminary Report on Patentability mailed Aug. 20, 2008 in International Patent Application No. PCT/US2004/013444, 7 pages.
WIPO, International Preliminary Examining Authority, International Preliminary Report on Patentability mailed Feb. 3, 2009 in International Patent Application No. PCT/EP2007/058025, 10 pages.
WIPO, European International Preliminary Examining Authority, Written Opinion mailed Feb. 2, 2009 in International Patent Application No. PCT/EP2007/058025, 9 pages.
United States Patent and Trademark Office, Final Office Action mailed Jan. 27, 2009 in U.S. Appl. No. 10/792,110, 8 pages.
United States Patent and Trademark Office, Office Action mailed Aug. 12, 2008 in U.S. Appl. No. 11/333,966, 34 pages.
United States Patent and Trademark Office, Office Action mailed Jul. 14, 2008 in U.S. Appl. No. 11/246,412, 18 pages.
United States Patent and Trademark Office, Office Action mailed May 28, 2008 in U.S. Appl. No. 10/792,110, 15 pages.
WIPO, European International Search Authority, International Search Report mailed Feb. 19, 2008 in International Patent Application No. PCT/EP2007/058025, 5 pages.
WIPO, U.S. International Search Authority, International Search Report mailed Jan. 29, 2008 in International Patent Application No. PCT/US2004/013444, 3 pages.
United States Patent and Trademark Office, Office Action mailed Mar. 27, 2008 in U.S. Appl. No. 11/337,618, 10 pages.
WIPO, U.S. International Preliminary Examining Authority, Written Opinion mailed Jan. 29, 2008 in International Patent Application No. PCT/US2004/013444, 7 pages.
European Patent Office, Examination Report dated Nov. 27, 2007 in European Patent Application No. EP 04 716 458.7-2310, 3 pages.
WIPO, U.S. International Preliminary Examining Authority, International Preliminary Report on Patentability mailed Aug. 29, 2007 in International Patent Application No. PCT/US2004/006391, 3 pages.
WIPO, International Preliminary Examining Authority, International Preliminary Report on Patentability mailed in International Patent Application No. PCT/US2005/036477, 4 pages.
WIPO, U.S. International Preliminary Examining Authority, Written Opinion mailed Sep. 28, 2006 in International Patent Application No. PCT/US2005/036477, 3 pages.
WIPO, U.S. International Search Authority, International Search Report mailed Sep. 28, 2006 in International Patent Application No. PCT/US2005/036477, 1 page.
United States Patent and Trademark Office, Notice of Allowance mailed Nov. 15, 2006 in U.S. Appl. No. 10/971,452, 6 pages.
WIPO, U.S. International Preliminary Examining Authority, International Preliminary Report on Patentability mailed Apr. 11, 2006 in International Patent Application No. PCT/US2004/035233, 3 pages.
United States Patent and Trademark Office, Office Action mailed Aug. 1, 2006 in U.S. Appl. No. 10/835,697, 14 pages.
United States Patent and Trademark Office, Final Office Action mailed Aug. 1, 2006 in U.S. Appl. No. 10/971,452, 8 pages.
WIPO, International Preliminary Examining Authority, International Preliminary Report on Patentability mailed Apr. 24, 2006 in International Patent Application No. PCT/US2004/035233, 4 pages.
United States Patent and Trademark Office, Office Action mailed Apr. 17, 2006 in U.S. Appl. No. 10/835,697, 6 pages.
United States Patent and Trademark Office, Notice of Allowance mailed Apr. 12, 2006 in U.S. Appl. No. 10/792,111, 14 pages.
WIPO, U.S. International Search Authority, International Search Report and Written Opinion mailed Nov. 29, 2005 in International Patent Application No. PCT/US2004/035233, 3 pages.
United States Patent and Trademark Office, Office Action mailed Jan. 12, 2006 in U.S. Appl. No. 10/971,452, 12 pages.
United States Patent and Trademark Office, Final Office Action mailed Dec. 27, 2005 in U.S. Appl. No. 10/792,111, 13 pages.
United States Patent and Trademark Office, Office Action mailed Nov. 23, 2005 in U.S. Appl. No. 10/971,452, 5 pages.
United States Patent and Trademark Office, Office Action mailed Sep. 19, 2005 in U.S. Appl. No. 10/192,402, 7 pages.
WIPO, U.S. International Preliminary Examining Authority, International Search Report and Written Opinion mailed Sep. 15, 2005 in International Patent Application No. PCT/US2004/006391, 4 pages.
United States Patent and Trademark Office, Office Action mailed Jun. 15, 2005 in U.S. Appl. No. 10/792,111, 12 pages.
United States Patent and Trademark Office, Office Action mailed Jun. 3, 2005 in U.S. Appl. No. 10/192,402, 4 pages.
United States Patent and Trademark Office, Office Action mailed Mar. 24, 2005 in U.S. Appl. No. 10/792,111, 5 pages.
WIPO, European International Search Authority, International Search Report mailed Mar. 11, 2005 in International Patent Application No. PCT/EP2004/012799, 6 pages.
United States Patent and Trademark Office, Final Office Action mailed Oct. 4, 2004 in U.S. Appl. No. 10/192,402, 6 pages.
WIPO, U.S. International Preliminary Examining Authority, International Preliminary Report on Patentability mailed Oct. 26, 2004 in International Patent Application No. PCT/US2004/006390, 5 pages.
WIPO, U.S. International Preliminary Examining Authority, International Search Report and Written Opinion mailed Sep. 2, 2004 in International Patent Application No. PCT/US2004/006390, 6 pages.
WIPO, U.S. International Preliminary Examining Authority, International Preliminary Examination Report mailed Feb. 23, 2004 in International Patent Application No. PCT/US2002/021774, 3 pages.
United States Patent and Trademark Office, Office Action mailed Mar. 29, 2004 in U.S. Appl. No. 10/192,402, 13 pages.
United States Patent and Trademark Office, Office Action mailed Nov. 7, 2003 in U.S. Appl. No. 10/192,402, 7 pages.
Nitta, T., "Radial Procedure and Beyond: Map-guided AF Surgery," *The third Annual Conference On the Surgical Treatment of Atrial Fibrillation*, Jun. 18-19, 2003, 36 pages.
WIPO, European International Search Authority, International Search Report mailed Nov. 7, 2002 in International Patent Application No. PCT/US2002/021774, 3 pages.
Damiano, Jr., R., "Alternative Energy Sources for Atrial Ablation: Judging the New Technology," *Ann Thorac Surg*, 2003;75:329-30, 21 pages.
Benussi, S. et al., "A tailored Anatomical Approach to Prevent Complications During Left Atrial Ablation," *Ann Thorac Surg*, 2003:75-1979-81, 3 pages.
Benussi, S. et al., "Surgical Ablation of Atrial Fibrillation Using the Epicardial Radiofrequency Approach: Mid-Term Results and Risk Analysis," *Ann Thorac Surg*, 2002;74:1050-7, 9 pages.
Natale, A., "Radiofrequency ablation of the pulmonary veins: Can it stop atrial fibrillation at its source?", *Cleveland Clinic Journal of Medicine*, vol. 53, No. 1, Jan. 2001, 5 pages.

(56) References Cited

OTHER PUBLICATIONS

Yang, M. et al., "Identification of Pulmonary Vein Stenosis After Radiofrequency Ablation for Atrial Fibrillation Using MRI," *Journal of Computer Assisted Tomography*, vol. 25, No. 1, Jan./Feb. 2001, 34-35, 3 pages.

Moubarak, J.B. et al., "Pulmonary Veins-Left Atrial Junction: Anatomic and Histological Study," *Pacing and Clinical Electrophysiology*, vol. 23, Nov. 2000, Part II, 1836-1838, 4 pages.

Benussi, S. et al., "A simple way to treat chronic atrial fibrillation during mitral valve surgery: the epicardial radiofrequency approach," *European Journal of Cardio-thoracic Surgery* 17 (2000) 524-529, 6 pages.

Shah, D.C. et al., "Catheter Ablation of Pulmonary Vein Foci for Atrial Fibrillation," *Thorac. Cardiovasc. Surg.* 47 (1999) (Supplement) 352-356, 7 pages.

Lesh, M.D. et al., "An Anatomic Approach to Prevention of Atrial Fibrillation: Pulmonary Vein Isolation with Through-the-Balloon Ultrasound Ablation (TTB-USA)," *Thorac. Cardiovasc. Surg.* 47 (1999) (Supplement) 347-351, 6 pages.

Haïssaguerre, M. et al., "Spontaneous Initiation of Atrial Fibrillation by Ectopic Beats Originating in the Pulmonary Vein," *N Engl J Med* 1998;339:659-66, vol. 339, Number, 9 pages.

Fieguth, H.-G. et al., "Inhibition of atrial fibrillation by pulmonary vein isolation and auricular resection—experimental study in a sheep model," *European Journal of Cardio-thoracic Surgery* 11 (1997) 714-721, 8 pages.

Cox, J.L. et al., "The surgical treatment of atrial fibrillation," *J Thorac Cardiovasc Surg* 1991;101:406-26, 21 pages.

Sandöe, E. et al., "Arrhythmia, Diagnosis and Management, A clinical Electrocardiographic Guide," *Fachmed AG* (1984), pp. 2-11, 13 pages.

Willert, H.-G. et al., "Reactions of the Articular Capsule to Wear Products of Artificial Joint Prostheses," *J. Biomed. Mater. Res.* vol. 11, pp. 157-164 (1977), 8 pages.

\* cited by examiner

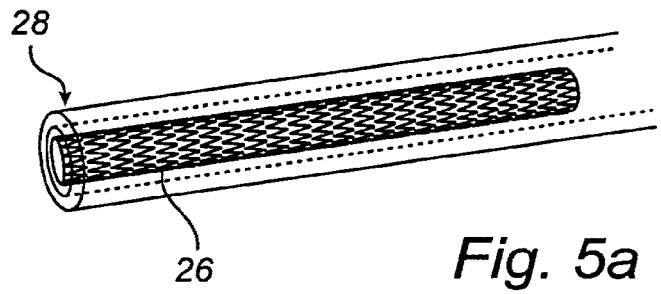
*Fig. 5a*
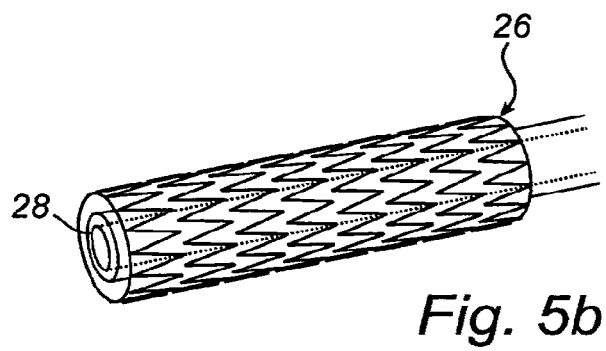
*Fig. 5b*
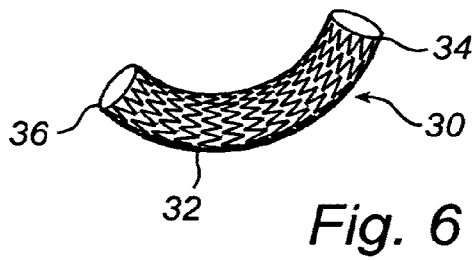
*Fig. 6*
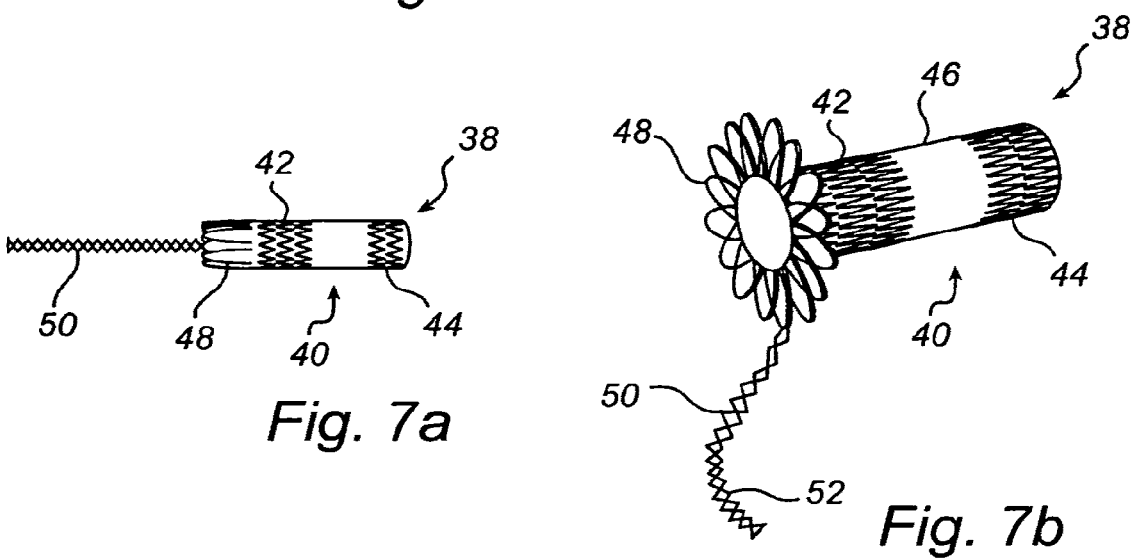
*Fig. 7a*
*Fig. 7b*

DEVICE, A KIT AND A METHOD FOR TREATMENT OF DISORDERS IN THE HEART RHYTHM REGULATION SYSTEM

RELATED APPLICATIONS

This application is a divisional of and claims priority to U.S. patent application Ser. No. 10/989,551, filed Nov. 17, 2004, now abandoned entitled A Device, A Kit And A Method For Treatment Of Disorders In The Heart Rhythm Regulation System, which claims priority to Swedish Provisional Application No. 0303017-8 filed Nov. 17, 2003, both of which are hereby incorporated herein by reference.

FIELD OF THE INVENTION

The present invention relates to treatment of disorders in the heart rhythm regulation system and, specifically, to a tissue lesion creating device, a kit of shape-changing devices and a method for treating such disorders.

BACKGROUND OF INVENTION

The circulation of blood in the body is controlled by the pumping action of the heart. The heart expands and contracts by the force of the heart muscle under impulses from the heart rhythm regulation system. The heart rhythm regulation system transfers an electrical signal for activating the heart muscle cells.

The normal conduction of electrical impulses through the heart starts in the sinoatrial node, travels across the right atrium, the atrioventricular node, the bundles of His and thereafter spread across the ventricular muscle mass. Eventually when the signal reaches the myocytes specialized in only contraction, the muscle cell will contract and create the pumping function of the heart (see FIG. 1).

The electrical impulses are transferred by specially adapted cells. Such a cell will create and discharge a potential over the cell membrane by pumping ions in and out of the cell. Adjacent cells are joined end-to-end by intercalated disks. These disks are cell membranes with a very low electrical impedance. An activation of a potential in a cell will propagate to adjacent cells thanks to the low impedance of the intercalated disks between the cells. While being at the embryonic stage, all heart muscle cells, the myocytes, have the ability to create and transfer electrical signals. During evolution the myocytes specialize and only those cells necessary for maintaining a stable heart-rate are keeping the ability to create and send electrical impulses. For a more thorough explanation of the propagation of electrical signals in the heart, see e.g. Sandöe, E. and Sigurd, B., *Arrhythmia, Diagnosis and Management, A Clinical Electrocardiographic Guide*, Fachmed AG, 1984.

The heart function will be impaired if there is a disturbance on the normal conduction of the electrical impulses. Atrial fibrillation (AF) is a condition of electrical disorder in the heart rhythm regulation system. In this condition, premature and fast signals irregularly initiating muscle contractions in the atria as well as in the ventricles will be started in ectopic sites, that is areas outside the sinoatrial node. These signals will be transmitted erratically all over the heart. When more than one such ectopic site starts to transmit, the situation becomes totally chaotic, in contrast to the perfect regularity in a healthy heart, where the rhythm is controlled from the sinoatrial node.

Atrial fibrillation is a very common disorder, thus 5% of all patients that undergo heart surgery suffer from AF. 0.4-2% of a population will suffer from AF, whereas 10% of the population over the age of 65 suffers from AF. 160 000 new cases occur every year in the US and the number of cases at present in the US is estimated to be around 3 million persons. Thus, treatment of atrial fibrillation is an important topic.

Typical sites for ectopic premature signals in AF may be anywhere in the atria, in the pulmonary veins (PV), in the coronary sinus (CS), in the superior vena cava (SVC) or in the inferior vena cava (JVC). There are myocardial muscle sleeves present around the orifices and inside the SVC, IVC, CS and the PVs. Especially around the orifice of the left superior pulmonary vein (LSPV) such ectopic sites are frequent, as well as at the orifice of the right superior pulmonary vein (RSPV). In AF multiple small circles of a transmitted electrical signal started in an ectopic site may develop, creating re-entry of the signal in circles and the circle areas will sustain themselves for long time. There may be only one ectopic site sending out signals leading to atrial flutter, or there may be multiple sites of excitation resulting in atrial fibrillation. The conditions may be chronic or continuous since they never stop. In other cases there may be periods of normal regular sinus rhythm between arrhythmias. The condition will then be described as intermittent.

In the chronic or continuous cases, the atrial musculature undergoes an electrical remodelling so that the re-entrant circuits sustain themselves continuously. The patient will feel discomfort by the irregular heart rate, sometimes in form of cannon waves of blood being pushed backwards in the venous system, when the atria contract against a closed arterio-ventricle valve. The irregular action of the atria creates standstill of blood in certain areas of the heart, predominantly in the auricles of the left and right atrium. Here, blood clots may develop. Such blood clots may in the left side of the heart get loose and be taken by the blood stream to the brain, where it creates disastrous damage in form of cerebral stroke. AF is considered to be a major cause of stroke, which is one of the biggest medical problems today.

Today, there are a few methods of treating the problems of disorders to the heart rhythm regulation system. Numerous drugs have been developed to treat AF, but the use of drugs is not effective to a large part of the patients. Thus, there has also been developed a number of surgical therapies.

Surgical therapy was introduced by Drs. Cox, Boineau and others in the late 1980s. The principle for surgical treatment is to cut all the way through the atrial wall by means of knife and scissors and create a total separation of the tissue. Subsequently the tissues are sewn together again to heal by fibrous tissue, which does not have the ability to transmit myocardial electrical signals. A pattern of cutting was created to prohibit the propagation of impulses and thereby isolate the ectopic sites, and thus maintain the heart in sinus rhythm. The rationale for this treatment is understandable from the description above, explaining that there must be a physical contact from myocyte to myocyte for a transfer of information between them. By making a complete division of tissue, a replacement by non-conductive tissue will prohibit further ectopic sites to take over the stimulation. The ectopic sites will thus be isolated and the impulses started in the ectopic sites will therefore not propagate to other parts of the heart.

It is necessary to literally cut the atria and the SVC and the IVC in strips. When the strips are sewn together they will give the impression of a labyrinth guiding the impulse from the sinoatrial node to the atrioventricular node, and the operation was consequently given the name Maze. The cutting pattern is illustrated in FIG. 2 and was originally presented in J L Cox, T E Canavan, R B Schuessler, M E Cain, B D Lindsay, C Stone, P K Smith, P B Corr, and J P Boineau, *The surgical* treatment of atrial fibrillation. II. Intraoperative electrophysiologic mapping and description of the electrophysiologic basis of atrial flutter and atrial fibrillation*, J Thorac Cardiovasc Surg, 1991 101: 406-426. The operation has a long-time success of curing patients from AF in 90% of the patients. However, the Maze operation implicate that many suture lines have to be made and requires that the cuts are completely sealed, which is a demanding task for every surgeon that tries the method. The operation is time consuming, especially the time when the patients own circulation has to be stopped and replaced by extracorporeal circulation by means of a heart-lung machine. Thus mortality has been high and the really good results remained in the hands of a few very trained and gifted surgeons.

The original Maze operation has therefore been simplified by eliminating the number of incisions to a minimum, still resulting in a good result in most cases. The currently most commonly used pattern of incisions is called Maze III (see FIG. 3).

Other methods of isolating the ectopic sites have also been developed recently. In these methods, the actual cutting and sewing of tissue has been replaced by methods for killing myocyte cells. Thus, one may avoid separating the tissue, instead one destroy the tissue by means of heat or cooling in the Maze pattern to create a lesion through the heart wall. The damaged myocyte tissue can not transfer signals any more and therefore the same result may be achieved. Still the chest has to be opened, and the heart stopped and opened. Further, the energy source has to be carefully controlled to affect only tissue that is to be destroyed.

A large number of devices have now been developed using various energy sources for destroying the myocyte tissue. Such devices may use high radio frequency energy, as disclosed in e.g. U.S. Pat. No. 5,938,660, or microwaves, ultrasound or laser energy. Recently, devices have been developed for catheter-based delivery of high radio frequency energy through the venous and or arterial systems. However, this has so far had limited success due to difficulties in navigation and application of energy and also late PV stenosis has been reported. Further, devices using cooling of tissue has used expanding argon gas or helium gas to create temperatures of −160° C. Using an instrument with a tip, tissue can be frozen and destroyed.

SUMMARY OF THE INVENTION

It is an object of the invention to provide a new device and method for treatment of disorders to the heart rhythm regulation system. It is a further object of the invention to provide a device and method that may be used without the need for open surgery or stopping the heart.

According to an aspect of the invention, there is provided a tissue lesion creating device for reducing undesired signal transmission in heart tissue. The device is structured and arranged to be inserted through the vascular system into a body vessel adjacent the heart and to be subsequently subjected to a change of shape in order to penetrate into said heart tissue.

Thanks to this aspect of the invention, the myocyte tissue may be treated by simply inserting a device that is able to change its shape into the vascular system of the heart. This may be done through the vascular system, making the insertion only slightly invasive. Thus, there is no need for stopping the heart or cutting or treating of the myocyte tissue with advanced or demanding methods. The invention provides an entirely new concept of treating disorders in the heart rhythm regulation system and for cutting the heart wall. The invention uses an inherent force in the device, which alters the shape of the device and thereby affects the tissue in the position where the device has been placed. The device is structured and arranged to change its shape in such a way that it will penetrate and cut through any tissue that is in the path of its change of shape. Thus, by setting the shape of the device properly and placing the device in a suitable position, the device may by its own inherent force penetrate the tissue that needs treatment. The tissue that is penetrated will be destroyed and start a healing process within the body. The tissue will then be replaced by fibrous tissue, which is not able to transmit electrical signals. Thus, the signal transmission in the treated heart tissue is reduced or blocked and the desired effect is achieved. Therefore, such devices could be used for accomplishing the creation of a cutting pattern for isolating ectopic sites causing disturbances to the heart rhythm regulation system.

The device may be structured and arranged to penetrate through a wall of the vessel into the heart tissue. In this way, the device will only need to be inserted into a desired position within the body vessel. Then, the device may itself penetrate the body vessel wall in order to access the heart tissue to be treated and thereafter the device may continue its change of shape to penetrate the heart tissue. The device may change shape such that it penetrates the body vessel wall in its entirety. Alternatively, the device changes shape such that only a part of the device will penetrate the vessel wall.

The device may have an initial elongate shape and the device is structured and arranged to change shape to expand its dimensions in a direction transversally to its elongate direction. Thanks to the elongate shape, the device may interact with a substantial portion of tissue, whereby the device will be stabilized and the risk of it being transported by the blood flow away from its desired position is reduced. Further, the device may readily be inserted to the desired position through the vascular system, while having a small crosssection, and then change its shape to increase its dimension in the transversal direction. Thus, tissue outside the vessel in the desired position may be treated.

The device may comprise a shape memory material. This is suitable for providing the ability of the device to perform the change of shape. The shape memory material may serve to maintain the device in a first state while the device is being inserted, the device in said first state being structured and arranged to be inserted into a body vessel adjacent the heart through the vascular system, and to transfer the device to a second state when the device has been inserted to a desired position within the vessel, the device in said second state being structured and arranged to strive to obtain a shape that at least partly extends outside the perimeter and the orifice of the vessel wall. Thus, the device presents an initial shape in the first state allowing the device to be inserted through the vascular system to a desired position in a body vessel. Further, the device is self-transferable to a second shape and, during the change of shape, the device will penetrate heart tissue. The shape memory material will give the device a strong inherent force, driving the device to perform the change of shape. Meanwhile, as long as the shape memory material is not activated it will retain its shape of the first state being suited for insertion into a body vessel. Thus, by not activating or by restraining the shape memory material until the device has been inserted into the desired position, the device may readily be inserted into the desired position through the vascular system. Further, when the shape memory material is activated, the device will strive towards a change of shape and will penetrate and destroy tissue on its path to the new shape.

The shape memory material may easily be activated, e.g. by assuming a raised temperature, which may be provided by the body temperature.

The device may comprise a transversely expandable tubular part. The device may then be structured and arranged to be subjected to a change of shape to expand the cross-section of the tubular part such that the tubular part circumferentially penetrates the vessel wall and thereafter penetrates the heart tissue outside the vessel wall. If this device is inserted into an artery or vein at its orifice into the heart, the circumferential expansion of the device will treat the heart wall tissue around the entire orifice. This is especially suitable, since the ectopic sites often are located around and adjacent the orifices of the pulmonary veins (PV). Further, the tubular form is suitable for insertion into the vascular system.

In an embodiment, the tubular part of the device is funnel-shaped. This implies that the cross-section of the tubular part is larger at one end and smaller at the other end. This feature of the device is also very suitable for devices that are inserted at an orifice of a vessel into the heart, since only a portion of the tubular part adjacent the heart wall near the orifice needs to penetrate tissue outside the vessel. Thus, the end that assumes a larger cross-section after the change of shape will be inserted closest to the orifice to penetrate the heart wall tissue around the orifice. Further, the other end of the tubular part may have an expanded cross-section that is so small that it stays in the inner layers of the vessel wall. This smaller end will then serve only to keep the device in place.

The tubular part may comprise at least two axially separated tubular portions, which are interconnected by a connecting member. These tubular portions may then be structured and arranged to change shape to expand to different diameters or be transversely expandable to different degrees. This may be used for the same purpose as the funnel-shape described above. Thus, at least one of the tubular portions may be structured and arranged to change shape to expand its diameter to correspond to the diameter of the vessel where it is placed. In this way, this tubular portion will only serve to keep the device in place. Another tubular portion may then change shape to penetrate the heart tissue for the treatment purposes. Further, the connecting member may be one or more bars or wires connecting the tubular portions.

An end of the tubular part may form an atrial end. The atrial end is structured and arranged to change shape to extend radially from the tubular part. When radially extended the atrial end will form a flange for fixing the device to the heart wall. A device being inserted at the orifice of a vessel into the heart may then comprise a flange, which may extend into the heart wall for improving the fixation of the device and also contributing to the treating of the heart wall tissue. In this way, the atrial end may serve to fixate a device that is inserted into a vein leading to the heart.

The atrial end may comprise a plurality of arches overlapping each other. In this way, several different parts of the atrial end contribute to the fixation of the device. Further, if each arch changes shape to extend into the heart wall tissue, the atrial end forms a dense pattern of treated heart wall tissue for effectively isolating ectopic sites.

The atrial end may form an annular flange when extending radially from the tubular part. Thus, the entire area around the orifice of the vessel into the heart may be treated, and a stable fixation may be accomplished.

In an embodiment, the device further comprises a cutting arm being structured and arranged to initially extend axially from the tubular part in order to be inserted into a heart atrium and said cutting arm being structured and arranged to change shape to extend radially from the tubular part. A cutting arm may create a lesion along a cutting line in the heart wall. Thus, a specific cut may be achieved and a specific portion of the heart wall may be treated. By inserting the cutting arm into a heart atrium, the cutting arm will initially be placed inside the heart wall, preferably in contact with the heart wall. By further appropriately positioning the tubular part, to which the cutting arm is connected, the cutting arm could strive to assume a shape, where it extends outside the heart wall. The cutting arm will then penetrate through the heart wall and thereby create an elongate lesion.

The cutting arm may have a form comprising at least one closed loop. The cutting arm will penetrate tissue forming a lesion corresponding to the form of the cutting arm. As the cutting arm comprises a closed loop, an islet of untreated tissue will be formed inside the closed loop. Mainly, the cutting arm will create a lesion, which will cause a line of scar tissue that represents an effective block against propagation of undesired electrical signals. Moreover, if there is an ectopic site present in the islet, this ectopic site will be effectively isolated.

The cutting arm may have a form comprising a plurality of closed loops arranged subsequently to each other in a longitudinal direction of the cutting arm. This implies that a dense pattern of treated tissue may be accomplished and several islets may be formed, possibly isolating ectopic sites. Further, one or more abutting islets create a line of scar tissue, representing an effective block against propagation of undesired electrical signals.

The device may comprise at least two cutting arms, which are structured and arranged to change shape to extend in different radial directions from the tubular part. This implies that lesions along different cutting lines may be formed in order to obtain a desired cutting pattern in the heart wall tissue.

The tubular part of the device may be structured and arranged to be inserted into the coronary sinus (CS). The tubular part may then, in a first state of the device before the device is subjected to a change of shape, strive towards a shape that is curved along its longitudinal direction to fit into the CS. Such a device may be arranged to change shape to expand mainly at the inside of the curve towards the heart wall. Hereby, a portion of the heart wall along the CS may be treated. Further, the device inserted into the CS may be arranged to form a support for a cutting arm extending from a tubular part inserted into a PV, after the cutting arm has performed its change of shape.

As used herein, the term "coronary sinus" implies not only the portion of the vein at its opening to the right atrium, but also the great cardiac vein extending from the right atrium for draining blood from the heart tissue.

The tubular part to be inserted into the CS may have a length corresponding to at least the distance between the two lower PVs. This implies that a substantial portion of the heart wall may be treated by the device inserted into the CS. Further, the CS may then serve as a support for cutting arms extending from tubular parts inserted in each of the lower PVs, respectively.

The cross-section of the tubular part to be inserted into the CS may at least partly be elliptic. In this way, the expansion mainly at the inside of the curve towards the heart wall may be achieved. Of course, devices to be inserted in other vessels may also present a tubular part having a cross-section that is at least partly elliptic. Further, the cross-section of the tubular parts may be varied infinitely to suit the area around the vessel to be treated.

The cutting device to be inserted into the CS may also comprise a cutting arm being structured and arranged to initially extend in an axial direction of the tubular part in order to be inserted into the CS and being structured and arranged to change shape to extend radially from the tubular part. Thus, a specific cut along a cutting line in the heart wall may be created from a device inserted into the CS.

An outside surface of the device may be provided with sharp edges. Thus, the ability of the device to penetrate through tissue is increased, ensuring that the device will perform its change of shape. All parts of a device, such as the tubular part, the atrial end, and the cutting arm as described above, may be provided with such sharp edges.

An outside surface of the device may also or alternatively be provided with drugs. The drugs may be adapted to increase a cutting effect through tissue. This will also increase the ability of the device to penetrate through tissue and treat the tissue. Also, the drugs may be adapted to prohibit a thickening of the wall of the vessel, in which the device is inserted.

The drug adapted to increase a cutting effect may be e.g. any one in the group of alcohol, glutaraldehyde, formaldehyde, and proteolytic enzymes like collagenase. Further, any combination of these drugs may be contemplated. These drugs will have a toxic effect on tissue and thereby permit an easier penetration of the device through tissue.

The drug adapted to prohibit a thickening of the vessel wall may be e.g. any one in the group of ciclosporin, taxiferol, rapamycin and tacrolimus. Further, any combination of these drugs may be contemplated. The penetration of the device through tissue in the body may cause a healing reaction in the body in the form of a local proliferative reaction in the tissue. As a result of a thickening of the vessel wall, the local proliferative reaction may cause a stenosis, which is a very dangerous situation in the PV. The drug adapted to prohibit a thickening of the vessel wall has an anti-proliferative effect, i.e. it will prohibit a local proliferative reaction and it will therefore prevent the thickening of the vessel wall.

Moreover, the drugs may include any one in the group of Endothelium Growth Factor, Heparin, amiodarone and sotalol. Endothelium Growth Factor and Heparin are drugs preventing thrombosis and increasing in-growth of endothelium on the endothelial surface of the vessel wall after penetration of the cutting device. Amiodarone and sotalol are drugs designed to treat arrhythmias. Also, other drugs with these or other effects may be contemplated.

The device may have a net-like shape formed of closed loops. The device will penetrate tissue forming a lesion corresponding to the form of the device having penetrated the tissue. As the device has a net-like shape, islets of untreated tissue will be formed inside the closed loop of the net. If there is an ectopic site present in an islet, this ectopic site will be isolated. This ensures that tissue is treated in a dense pattern. Further, the net-like nature of the device also facilitates the penetration of the device through tissue compared to a device having a complete surface.

The device may be at least partly bioresorbable. Thus, the device may first be inserted to a desired position and change its shape to penetrate and destroy tissue in order to treat disorders to the heart rhythm regulation system. Thereafter, the desired effect of the device has been achieved and there is no further need for the device being maintained in the body. Thus, the device may be designed in a bioresorbable material to thereafter be absorbed and repelled by the body or at least certain parts located in especially inconvenient places may be absorbed.

The device may be made of a shape memory polymer. The shape memory polymer may provide an inherent force to accomplish the change of shape, when the device has been inserted to a desired position. Further, a shape memory polymer may be resorbed by the body. Alternatively, the device may be made of Nitinol or any other metal alloy, which also has a shape memory for providing the inherent force to accomplish the change of shape. Examples of other shape memory alloys that may be used are alloys made of titanium-palladium-nickel, nickel-titanium-copper, gold-cadmium, iron-zinc-copper-aluminium, titanium-niobium-aluminium, uranium-niobium, hafnium-titanium-nickel, iron-manganese-silicon, nickel-iron-zinc-aluminium, copper-aluminium-iron, titanium-niobium, zirconium-copper-zinc or nickel-zirconium-titanium. The device may alternatively be formed to exhibit an elasticity for providing the inherent force. Thus, the metal alloy may be e.g. stainless steel, a titanium alloy or a magnesium alloy. The metal alloy may also be designed to be resorbed by the body. This is possible for e.g. magnesium alloys.

According to another aspect of the invention, there is provided a kit of shape-changing devices for treatment of disorders in the heart rhythm regulation system. The kit comprises shape-changing devices, which each has a first and a second state, wherein the device in the first state has such dimensions as to be insertable to a desired position within the vascular system, and wherein the device is capable of changing shape to the second state when located at said desired position. In the second state, the device has a tubular part, which strives to a diameter that is larger than the diameter of the vessel at the desired position, whereby the device will become embedded into the tissue surrounding the vessel at the desired position and destroy the tissue in order to prevent it from transmitting electrical signals. At least one of the shape-changing devices is adapted to be inserted to a desired position at the orifice of a pulmonary vein in the heart and at least one of the shape-changing devices is adapted to be inserted to a desired position in the coronary sinus.

According to this aspect of the invention, a kit of shape-changing devices that may penetrate heart tissue provides a possibility of placing the devices properly in vessels adjacent the heart in order to penetrate surrounding tissue and, thus, create lesions for affecting the transmission of electrical signals in the tissue. The kit may provide devices adapted to be inserted such that a suitable pattern of lesions may be created through the heart wall. The kit may comprise various numbers of shape-changing devices depending on how severe the electrical disorder of the patient is. In some cases, it may be sufficient to treat the PV and the CS, since the disease often starts in or around the PV. The shape-changing devices inserted into the PV and the CS may be expanded in the patient to come in contact with each other. Then, the expansion will be stopped. Further, this ensures that all tissue between the PV and the CS has been cut completely through and thus effectively the entire heart wall between the PV and the CS has been cut through creating a lesion between the PV and the CS, and lesions around the PV and the CS. Similar contacts between other shape-changing devices in the kit may be established between PVs and the superior vena cava (SVC) or inferior vena cava (IVC) or between the IVC and the CS.

The shape-changing device adapted to be inserted into the CS may extend along a substantial length of the CS in order to be able to create an elongate lesion in the heart wall adjacent the CS.

The shape-changing device that is adapted to be inserted into the PV may comprise an arm, which in the second state is arranged to contact the shape-changing device in the CS. Thus, a lesion may be created from the PV to the CS, when the arm changes shape. Further, the contact between the arm and the device in the CS fixates the position of the arm.

The arm may comprise a trough in an area to come in contact with the shape-changing device in the CS. This implies that the arm may extend past the CS to further create a lesion in the heart wall from the CS towards the mitral valve.

At least one of the shape-changing devices in the kit may be adapted to be inserted into the IVC. Also, at least one of the shape-changing devices in the kit may be adapted to be inserted into the SVC. Thus, the treated pattern may extend around the IVC and the SVC as well.

Further, at least one of the shape-changing device that is adapted to be inserted into the SVC and the shape-changing device that is adapted to be inserted into the IVC may comprise an arm, which in the second state is arranged to form a connection between these shape-changing devices. Thus, a lesion in the heart wall between the SVC and the IVC may be created.

The kit may comprise four shape-changing devices, each being adapted to be inserted into a respective PV. These shape-changing devices may treat the tissue around each PV. These areas are typical locations for ectopic sites.

Further, at least one of the shape-changing devices being adapted to be inserted into a PV may comprise an arm, which in the second state is arranged to contact the shape-changing device in another PV. Thus, a lesion between the PVs may be formed in order to further isolate the ectopic sites and create a cutting pattern that may effectively treat disorders to the heart rhythm regulation system.

At least one of the shape-changing devices in the kit may be adapted to be inserted into the left atrial appendage (LAA). This shape-changing device may be used for isolating the LAA totally from electrical contact with the other parts of the heart.

Further, the shape-changing device that is adapted to be inserted into the LAA may comprise an arm, which in the second state is arranged to contact the shape-changing device in a PV.

The shape-changing device that is adapted to be inserted into the LAA may comprise a film, which covers an end of the tubular shape of the device in the second state. Thus, the shape-changing device may be inserted with the end of the tubular shape of the device covering the connection between the LAA and the rest of the left atrium of the heart. In this way, the LAA is excluded from the blood circulating in the heart. Since the LAA is not needed for a satisfactory function of the heart, this will not affect the function of the heart. Further, an exclusion of the LAA effectively prohibits thrombus migration from the LAA, which may otherwise send embolies to the brain causing cerebral strokes.

At least one of the shape-changing devices in the kit may be adapted to be inserted into the right atrial appendage.

According to a further aspect of the invention, there is provided a method for treatment of disorders in the heart rhythm regulation system. The method comprises inserting a tissue lesion creating device through the vascular system to a desired position in a body vessel, and providing a change of shape of the tissue lesion creating device at said desired position to penetrate heart tissue adjacent said body vessel.

According to this aspect of the invention, a method is provided, whereby disorders to the heart rhythm regulation system may be treated without the need for stopping the heart or exceptional surgical skills for creating lesions in the heart wall. By simply inserting a shape-changing device to a desired position through the vascular system, the lesions through the heart wall may be created by means of the change of shape of the devices. The insertion of a shape-changing device may be accomplished by means of a catheter according to conventional methods. Further, by releasing the shape-changing device out of the catheter, it may change its own shape without requiring further controlling by a surgeon. The shape-changing devices may be designed beforehand to create a desired pattern of lesions for isolating ectopic sites in the heart wall. Thus, the surgeon need only insert the shape-changing devices to their correct positions. This method is only slightly invasive, since it is intended to be inserted just by means of skin puncture, and requires no surgical skills.

The method may further comprise restraining the tissue lesion creating device in an insertion shape during the inserting of the tissue lesion creating device. Thus, it may be ensured that the tissue lesion creating device maintains an insertion shape until it has been positioned at the desired position.

The restraining of the tissue lesion creating device may comprise keeping the tissue lesion creating device inside a tube. The tube will then prohibit the tissue lesion creating device from expanding.

The restraining of the tissue lesion creating device may also or alternatively comprise cooling the tissue lesion creating device. Thus, the temperature of the tissue lesion creating device may be held below a transition temperature trigging a change of shape of the tissue lesion creating device.

The method may further comprise releasing a restrain on the tissue lesion creating device when it has been inserted into the desired position for allowing said change of the shape of the tissue lesion creating device. The restrain may be released by withdrawing a tube holding the tissue lesion creating device in an insertion shape or by suspending the cooling of the tissue lesion creating device. This release may control the initiation of the change of shape of the tissue lesion creating device.

According to a further aspect of the invention, there is provided a medical device which is structured and arranged to be inserted into a body vessel and subsequently change shape therein. The medical device is structured and arranged to change shape to extend at least partly outside the perimeter or orifice of an outer wall of said vessel. This medical device may be used to penetrate tissue outside the vessel and thereby e.g. destroy heart tissue for creating a block against propagation of undesired electrical signals in the heart.

BRIEF DESCRIPTION OF THE DRAWINGS

The invention will now be described in further detail by way of example under reference to the accompanying drawings, on which:

FIGS. 4a-4c are perspective schematic views of a tissue lesion creating device according to an embodiment of the invention, wherein FIG. 4a shows the tissue lesion creating device in a first, temporary shape, FIG. 4b shows the tissue lesion creating device in a second, permanent shape, and FIG. 4c illustrates the tissue lesion creating device having sharp edges;

FIGS. 5a-5b show the tissue lesion creating device of FIGS. 4a-4b inserted in a body vessel;

FIGS. 6-12 show different embodiments of the tissue lesion creating device;

FIGS. 16-23 are schematic views of the heart showing tissue lesion creating devices inserted into different blood vessels adjacent the heart and illustrating cutting patterns achieved by these tissue lesion creating devices, wherein FIGS. 16-17 and 22-23 show a cross-section that has been cut through the atria of the heart and FIGS. 18-21 show the atria of the heart from the outside of the heart seen from behind;

FIGS. 24a-24b shows a cross-section of the left atrial appendage and a tissue lesion creating device inserted into the left atrial appendage, wherein FIG. 24a shows the tissue lesion creating device before a change of shape has started and FIG. 24b shows the tissue lesion creating device after the change of shape;

DETAILED DESCRIPTION OF A PREFERRED EMBODIMENT

Figure 1:
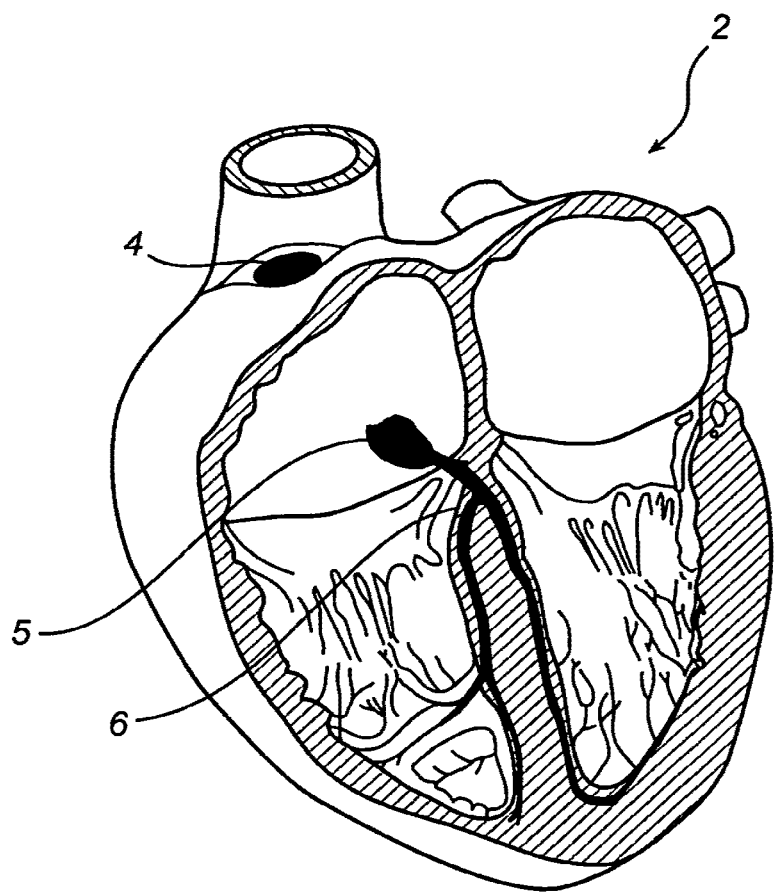
FIG. 1 is a schematic view of the transmission of electrical signals in the heart.
Figure 2:
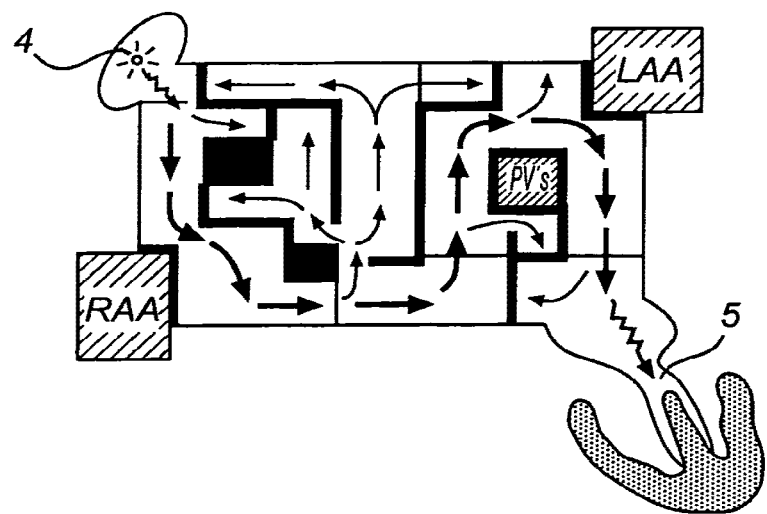
FIG. 2 is a schematic view of a pattern of cutting tissue of the heart wall according to the Maze-procedure for treating disorders to the heart rhythm regulation system.
Figure 3:
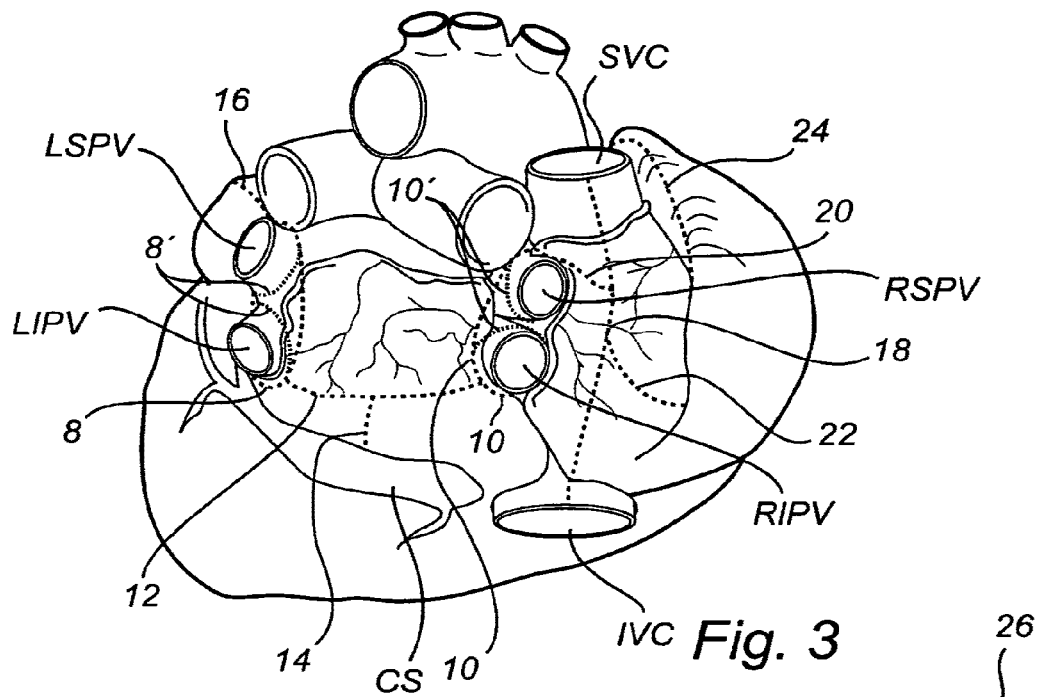
FIG. 3 is a schematic view of a simplified pattern according to the Maze III-procedure, wherein the heart is seen from behind.

Referring now to FIGS. 1-3, the problems of disorders to the heart rhythm regulation system and the leading current method of treating these problems will be described. In FIG. 1, a heart 2 is shown and the controlling of the heart rhythm is indicated. The heart rhythm is normally controlled from the sinoatrial node 4. The sinoatrial node 4 transmits electrical signals which are propagated through the heart wall by means of special cells forming an electrical pathway. The electrical signals following the electrical pathway will coordinate the heart muscle cells for almost simultaneous and coordinated contraction of the cells in a heart atrium and heart ventricle. The normal conduction of electrical impulses through the heart starts in the sinoatrial node 4, travels across the right atrium, the atrioventricular node 5, the bundles of His 6 and thereafter spread across the ventricular muscle mass. In a disordered situation, electrical signals are started in heart cells outside the sinoatrial node 4, in so called ectopic sites. These electrical signals will disturb the coordination of the heart muscle cells. If several ectopic sites are present, the signal transmission becomes chaotic. This will be the cause of arrhythmic diseases, such as atrial fibrillation and atrial flutter.

An existing method for treating these diseases is based on isolating the ectopic sites in order to prevent the electrical signals started in these ectopic sites to propagate in the heart wall. Thus, the heart wall is cut completely through for interrupting the coupling between cells that transmit erratic electrical signals. The thus created lesion will be healed with fibrous tissue, which is unable to transmit electrical signals. Thus, the path of the electrical signals is blocked by this lesion. However, since the location of the ectopic sites may not always be known and may be difficult to determine or since there might be multiple ectopic sites, a special cutting pattern has been developed, which will effectively isolate ectopic sites. Thus, the same pattern may always be used regardless of the specific locations of the ectopic sites in each individual case. The procedure is called the "Maze"-procedure in view of the complicated cutting pattern. In FIG. 2, the Maze-pattern is illustrated.

However, as is evident from FIG. 2, the cutting pattern is extensive and complex and requires a difficult surgery. Thus, the Maze-pattern has been evolved in order to minimize the required cuttings and simplify the pattern as much as possible. Currently, a Maze III-pattern is used, as shown in FIG. 3. This pattern is not as complicated, but would still effectively isolate the ectopic sites in most cases. The Maze III-pattern comprises a cut 8 around the left superior pulmonary vein (LSPV) and the left inferior pulmonary vein (LIPV) and a corresponding cut 10 around the right superior pulmonary vein (RSPV) and the right inferior pulmonary vein (RSPV); a cut 12 connecting the two cuts 8 and 10 around the pulmonary veins (PV); a cut 14 from this connecting cut to the coronary sinus (CS); a cut 16 from the left PVs to the left atrial appendage; a cut 18 from the inferior vena cava (IVC) to the superior vena cava (SVC); a cut 20 connecting the cut 10 around the right PVs and the cut 18 between the IVC and the SVC; a cut 22 from the cut 18 between the IVC and the SVC along the right lateral atrium wall; and a cut 24 isolating the right atrial appendage. Thus, a pattern, which is less complex and which effectively isolates the ectopic sites, has been established. In some cases, all cuts may not be needed. For example, the occurrence of ectopic sites often starts around the orifices of the PVs and, therefore, it may be sufficient to make the cuts 8, 10 around the PVs. Further, as indicated with the lines 8' and 10', the cuts around the PVs may be done along each PV orifice instead of in pairs.

According to the invention, there is provided a possibility of cutting through the heart wall in a new manner. Thus, a similar pattern to the Maze III-pattern should also be achieved according to this new manner. However, as mentioned above, it may not in all cases be required that all cuts of the Maze III-pattern are made.

Figure 4A:
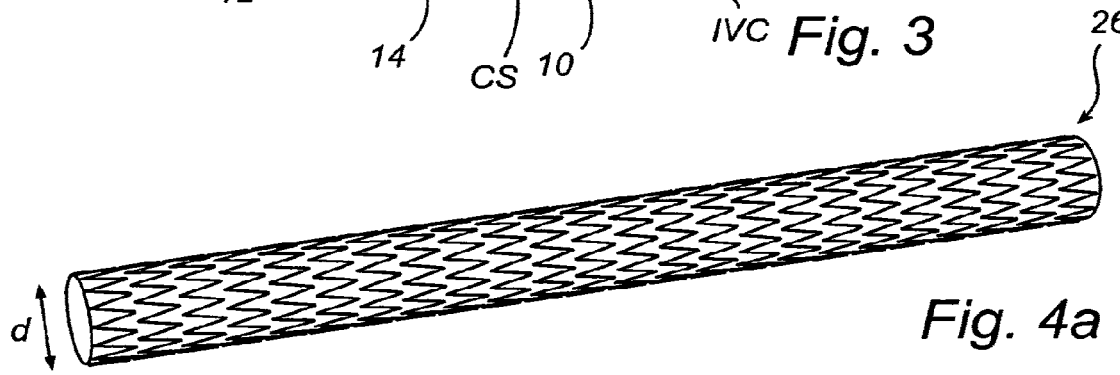
Figure 4B:
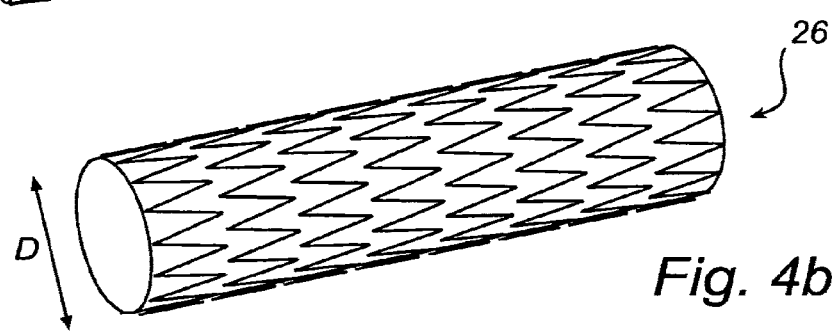

Referring now to FIGS. 4-5, a heart wall tissue lesion creating device 26 according to an embodiment of the invention will be described and the new manner of performing the cuts through the heart wall will be explained. The heart wall tissue lesion creating device 26 (hereinafter called cutting device) is shown in FIG. 4a in a first state, in which the cutting device 26 is tubular and has a first diameter d. The cutting device 26 is shown in FIG. 4b in a second state, in which the cutting device 26 is tubular and has a second diameter D, which is larger than the first diameter d. The cutting device 26 is formed of a shape memory material, which has the ability of memorizing a permanent shape that may significantly differ from a temporary shape. The shape memory material will transfer from its temporary to its memorized, permanent shape as a response to a suitable stimulus. The stimulus may be exposure to a raised temperature, such as a temperature above e.g. 30° C. that may be caused by the body temperature. The stimulus may suitably be combined with the release of a restraining means, which may keep the shape memory material from assuming its permanent shape.

The shape memory material allows designing a cutting device 26 that may be contracted into a small, temporary shape before insertion into a patient. Thus, the cutting device 26 may be inserted in this temporary shape to the heart of a patient through the vascular system. The temporary shape of the cutting device 26 is also flexible, whereby guiding the cutting device 26 through the vascular system is facilitated. This insertion of the cutting device 26 may be performed with well-known percutaneous catheter techniques. This is an unaggressive procedure and may be performed on a beating heart. Thus, the cutting device 26 may readily be positioned at a desired position within the vascular system adjacent heart wall tissue to be treated. The cutting device 26 may then be allowed to transfer to its memorized, permanent shape when inserted to the desired position in a blood vessel.

As shown in FIG. 5a, the cutting device 26 is inserted in its temporary shape in a desired position within a blood vessel 28. As a response to a stimulus, e.g. the body temperature, the cutting device 26 will then strive towards changing its shape and obtaining the permanent shape. The memorized, permanent shape of the cutting device 26 will not fit into the blood vessel 28, whereby the cutting device 26 will force itself through surrounding tissue for obtaining the permanent shape, as shown in FIG. 5b. In this way, the cutting device 26 will first penetrate the vessel wall and thereafter tissue surrounding the blood vessel 28. Tissue cells that are penetrated will be killed, which will start a healing reaction in the body. Where the cutting device 26 is placed in a desired position to change shape through heart wall tissue, cells that are able to transmit electrical signals may thus be killed. The healing process will not restore the ability to transmit electrical signals and, therefore, the cutting device 26 will reduce the ability of transmitting electrical signals through the heart wall. By placing several cutting devices intelligently and designing the permanent shape of the cutting devices 26 accordingly, the cutting devices 26 may penetrate heart wall tissue to create a pattern of cuts corresponding to the Maze III-pattern.

An example of a shape memory material is Nitinol, which is an alloy composed of nickel (54-60%) and titanium. Small traces of chrome, cobalt, magnesium and iron may also be present. This alloy uses a martensitic phase transition for recovering the permanent shape. Shape memory materials may also be formed of shape memory polymers, wherein the shape-memory effect is based on a glass transition or a melting point. Such shape memory polymers may be produced by forming polymers of materials or combinations of materials having suitable properties. For example, a shape memory polymer may be created of oligo(e-caprolactone) dimethacrylate combined with n-butyl acrylate. Also, biodegradable or bioresorbable materials may be used for forming these shape memory polymers. In this way, the cutting device 26 may be designed such that it will be degraded or absorbed by the body after it has performed its change of shape. For example, a polylactic acid polymer and/or a polyglycolic acid polymer, poly (e-caprolactone) or polydioxanone may be used for forming a shape memory polymer that is biodegradable. A special feature of the resorbable shape memory polymers is that these will disappear from the tissue after having had its function, limiting potential negative effects of otherwise remaining polymer or Nitinol materials, such as perforations and damage to other adjacent tissues, like lungs, oesophagus and great vessels like the aorta.

The cutting device 26 may alternatively be formed to exhibit an elasticity such that it has a strive towards its permanent shape. This may be accomplished by forming the cutting device 26 to a spiral-shape in e.g. stainless steel or a magnesium alloy which is biodegradable.

The cutting device 26 may be tubular in both its temporary shape and its permanent shape, as shown in FIGS. 4-5. However, the shape memory may be used for bringing the cutting device 26 between any shapes. Some examples of shapes that are at least not entirely tubular will be given below. The shape of the cutting device 26 in its first state is preferably compact to facilitate insertion of the cutting device 26 through the vascular system. Thus, a tubular shape is suitable, but other shapes may be conceivable. Further, the shape of the cutting device 26 in its second state is designed such that the change of shape will provide penetration of specific heart tissue in order to block propagation of undesired electrical signals. Also, the shape of the cutting device 26 in its second state may be adjusted for fixing the cutting device 26 to its desired position within the body.

The cutting device 26 may be constructed of a net; i.e. its shape may comprise meshes or loops. This implies that a solid surface need not penetrate tissue, whereby the penetration through tissue and the forming of different shapes of the cutting device 26 will be facilitated.

Figure 4C:
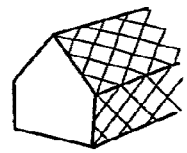

The edges of the cutting device 26 facing the tissue to be penetrated may be made especially sharp to increase its effectiveness, as illustrated in FIG. 4c. Another feature is to cover the surface towards the tissue to be penetrated with drugs that increase the cutting effect or prohibit the thickening of the wall of the vessel in which the device is inserted. Examples of such drugs are ciclosporin, taxiferol, rapamycin, tacrolimus, alcohol, glutaraldehyde, formaldehyde, and proteolytic enzymes like collagenase. Collagenase is effective in breaking down tissue and especially fibrin tissue, which is otherwise difficult to penetrate. Therefore, covering the surface of the cutting device 26 with collagenase would particularly speed up the process of penetrating tissue. The drugs are attached to the surface of the cutting device 26 according to well-known methods of attaching drugs to medical devices. One such method is embedding drugs into or under layers of polymers, which cover the surface. Of course, other methods may be used. Similarly, drugs preventing thrombosis and increasing in-growth of endothelium on the endothelial surface after penetration of the cutting device 26 may be attached to the cutting device 26. Such drugs would be e.g. Endothelium Growth Factor, and Heparin. Also, other drugs designed to treat arrhythmias may be attached to the cutting device surface. Such drugs are e.g. amiodarone and sotalol.

Preferably, the inside of the cutting device 26 inserted into a blood vessel will be in contact with the blood stream inside the blood vessel. Such inside surface of the cutting device 26 may as well be covered with antithrombotic drugs. Such drugs would be e.g. Heparin, Klopidogrel, Enoxaparin, Ticlopidin, Abciximab, and Tirofiban.

Another way to increase the effectiveness of the cutting device 26 is to attach a metallic part of the cutting device 26 to electrical currency, which would provide a heating of the cutting device 26. Thereby, tissue may also be killed by this heating, enhancing the effect of the cutting device 26. Further, the force driving the change of shape will also be increased, speeding up the shape change of the cutting device.

Referring now to FIGS. 6-12, cutting devices that are specifically suited for insertion into specific blood vessels will be described. All or some of these cutting devices may be delivered in a kit to be used for treatment of a disorder of the heart rhythm regulation system. Alternatively, the cutting devices may be delivered separately. Then, the required cutting devices for an operation may be assembled for each specific patient or for a specific disease pattern. The cutting devices may also be provided in different sizes to suit the size of the heart and the vessels of the patient. Thus, a complete kit is assembled from devices designed to fit to the anatomical conditions of the actual treatment locations in order to achieve optimal results.

Referring now to FIG. 6, a first cutting device 30 adapted to be inserted into the CS is shown. This first cutting device 30 has a tubular part 32, which is pre-bent to assume a curved shape to fit to the curvature of the CS. Thus, the first cutting device 30 will assume a curved temporary shape within the CS. Further, the cross-section of the first cutting device 30 is smaller in a distal end 34 to be inserted furthest into the CS than at a proximal end 36 to be placed at the orifice of the CS. The cross-section of the first cutting device 30 may be elliptic or circular or may vary along the length of the cutting device 30. The first cutting device 30 may be designed to change shape such that the cross-section of the first cutting device 30 is mainly expanded at the inside of the curve towards the heart wall. Thus, the first cutting device 30 will penetrate the heart wall tissue adjacent the CS. Moreover, the first cutting device 30 has a length of at least the distance between the two inferior PVs. It can also be designed to cover the distance from the orifice of the CS and past the LIPV. The first cutting device 30 may serve as support for other cutting devices inserted into other blood vessels adjacent the heart, as explained in more detail later on. In this case, it may suffice that the first cutting device 30 is fixated into the CS wall. There may also not be any need for the first cutting device 30 penetrating heart tissue itself, when treating the PV orifices solely. The first cutting device 30 may also comprise one or more cutting arms (not shown), which, in the temporary shape of the first cutting device 30, extend along the tubular part 32 or in an axial direction of the tubular part 32. Further, the first cutting device 30 may be arranged to change shape such that the one or more cutting arms extend in a radial direction from the tubular part 32. Thus, during the change of shape, the one or more cutting arms will penetrate through heart tissue adjacent the CS.

Referring now to FIGS. 7a-b, a second cutting device 38 adapted to be inserted into the LIPV is shown. In FIG. 7a, the second cutting device 38 is illustrated in a contracted, temporary shape, and in FIG. 7b, the second cutting device 38 is illustrated in an expanded state. This second cutting device 38 is adapted to be inserted at the orifice of the LIPV into the heart. The second cutting device 38 has a tubular part 40. As shown in FIGS. 7a-b, the tubular part 40 may comprise two or more portions. A first portion 42 of the tubular part 40 to be inserted closest to the LIPV orifice is arranged to change shape to circumferentially penetrate the LIPV wall and penetrate heart wall tissue around the LIPV. Thus, an effective block against propagation of undesired electrical signals is created around the orifice of the LIPV. A second portion 44 of the tubular part 40 is arranged to change shape to abut the vessel wall or only penetrate into the vessel wall. Thus, this second portion 44 will only serve to stabilize the second cutting device 38 in the axial direction and it may not be needed. The first 42 and second portions 44 of the tubular part 40 are interconnected by a connecting member 46, in the form of bars or wires. The first portion 42 may be funnel-shaped having a larger diameter at the end closest to the orifice of the LIPV. The funnel-shape will partly compensate for the increasing diameter of the LIPV towards the orifice. However, the diameter of the funnel-shaped first portion 42 may increase to a larger extent than the LIPV towards the orifice, whereby the second cutting device 38 will penetrate deeper into the heart tissue at the orifice end. Further, the smaller end of the funnel-shaped first portion 42 may be arranged to merely penetrate into or abut the vessel wall for stabilizing the second cutting device 38 in its axial direction. The first portion 42 of the tubular part 40 may extend from the orifice of the LIPV inside the heart to a position outside the heart wall, whereby the smaller end of the funnel-shaped first portion is arranged outside the heart wall. Thus, the first portion 42 may still penetrate through heart tissue throughout the entire thickness of the heart wall, even though the smaller end of the funnel-shaped first portion merely penetrates into or abuts the vessel wall.

The tubular part 40 is typically arranged to change shape to penetrate a circular area of tissue around and adjacent the LIPV. However, the tubular part 40 may also be arranged to change shape to expand to such a degree that it would come in contact with the first cutting device 30 inserted into the CS, whereby the heart tissue between the LIPV and the CS will be effectively treated. Then, the first 30 and the second cutting devices 38 in contact with each other will stabilize each other's positions.

The end of the tubular part 40 forms an atrial end 48, which is arranged to be inserted extending into the heart atrium when the second cutting device 38 is inserted into its desired position. Thus, as shown in FIG. 7a, during insertion of the second cutting device 38, the atrial end 48 will extend in an axial direction of the tubular part 40. However, when the second cutting device 38 changes shape the atrial end 48 will be folded outwardly extending in a radial direction to the tubular part 40, as shown in FIG. 7b. The atrial end 48 will during its change of shape penetrate into the heart wall for fixing the position of the second cutting device 38 and for forming a block against undesired electrical signals around the orifice of the LIPV. This atrial end 48 may be formed of, for instance, a multiple of arches overlapping each other. Each such arch will penetrate through a piece of tissue adjacent the LIPV orifice and leave a small islet of separated tissue, after having penetrated through the tissue.

The second cutting device 38 may also comprise a cutting arm 50. The cutting arm 50 is attached to the end of the tubular part 40 to be inserted closest to the LIPV orifice. In the temporary shape of the second cutting device 38, as shown in FIG. 7a, the cutting arm 50 extends in an axial direction of the tubular part 40 for facilitating insertion of the second cutting device 38. In the permanent shape of the second cutting device 38, the cutting arm 50 extends in a radial direction of the tubular part 40, as shown in FIG. 7*b*. When the second cutting device 38 is placed in its desired position, the cutting arm 50 will extend into the heart atrium. Thus, during the change of shape of the second cutting device 38, the cutting arm 50 will penetrate through the heart wall tissue to assume a position extending radially from the tubular part 40. This effect of the cutting arm 50 will be explained in more detail below with reference to FIGS. 13-15. The cutting arm 50 will create a line blocking propagation of undesired electrical signals in the heart wall. Thus, the cutting arm 50 could make cutting lines for forming the desired cutting pattern. The cutting arm 50 of the second cutting device 38 may be arranged to make a cut from the LIPV to the CS. Thus, the cutting arm 50 could come in contact with the first cutting device 30 inserted into the CS, which would fixate the position of the cutting arm 50. This cutting arm 50 could also comprise a trough 52 in the portion of the cutting arm 50 that will contact the first cutting device 38. This ensures that the cutting arm 50 beyond the trough 52 may extend through the heart wall from the CS to the mitral valve. The second cutting device 38 may also have further cutting arms {not shown} to be extended towards any of the other PVs.

The cutting arm is constructed of sequential loops in a longitudinal direction of the arm. As these loops penetrate through the heart wall tissue, closed loops of lesion lines will be formed, creating islets of untreated tissue inside them. The lesion lines will present a block of propagation of electrical signals.

Figures 8, 9:
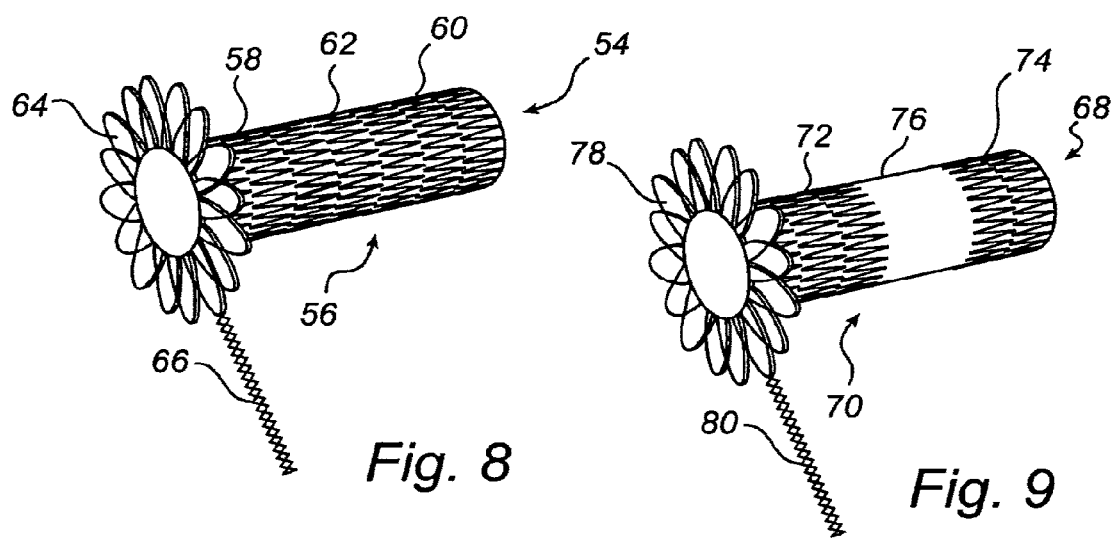

Referring now to FIG. 8, a third cutting device 54 adapted to be inserted into the RIPV is shown. This third cutting device 54 presents similar features as the second cutting device 38. Thus, the third cutting device 54 also comprises a tubular part 56, which also may consist of two or more tubular portions 58, 60, which are interconnected by a connecting member 62. The tubular part 56 of the third cutting device 54 presents similar features as the tubular part 40 of the second cutting device 38. The third cutting device 54 also comprises an atrial end 64, similar to the atrial end 48 of the second cutting device 38. Moreover, the third cutting device 54 also comprises a cutting arm 66, similar to the cutting arm 50 of the second cutting device 38. This cutting arm 66 is arranged to change shape in order to extend radially from the tubular part 56 towards the CS and come in contact with the first cutting device 30 inserted into the CS close to the orifice of the CS. The cutting arm 66 of the third cutting device 54 is normally shorter than the cutting arm 50 of the second cutting device 38 permitting adaptation to the different distance between the third cutting device 54 and the CS. Further, the cutting arm 66 of the third cutting device 54 need not have a trough, since, in this case, there is no need of treating heart tissue beyond the CS. The third cutting device 54 may also comprise other cutting arms (not shown) extending towards any of the other PVs.

Referring now to FIG. 9, a fourth cutting device 68 adapted to be inserted into the LSPV is shown. This fourth cutting device 68 presents similar features as the second and third cutting devices 38, 54. Thus, the fourth cutting device 68 also comprises a tubular part 70, which may consist of two or more tubular portions 72, 74, which are interconnected by a connecting member 76. The tubular part 70 of the fourth cutting device 68 presents similar features as the tubular part 40, 56 of the second and third cutting devices 38, 54. The fourth cutting device 68 also comprises an atrial end 78, similar to the atrial end 48, 64 of the second and third cutting devices 38, 54. Moreover, the fourth cutting device 68 also comprises a cutting arm 80, similar to the cutting arm 66 of the third cutting device 54. This cutting arm 80 is arranged to change shape in order to extend radially from the tubular part 70 towards the LIPV and come in contact with the second cutting device 38 inserted into the LIPV. The cutting arm 80 of the fourth cutting device 68 is normally very short permitting adaptation to the short distance between the LSPV and the LIPV, which is typically a few millimeters to a centimeter. The fourth cutting device 68 may also comprise another cutting arm (not shown), which after the change of shape of the fourth cutting device 68 would extend towards the left atrium appendage orifice.

Figures 10, 11:
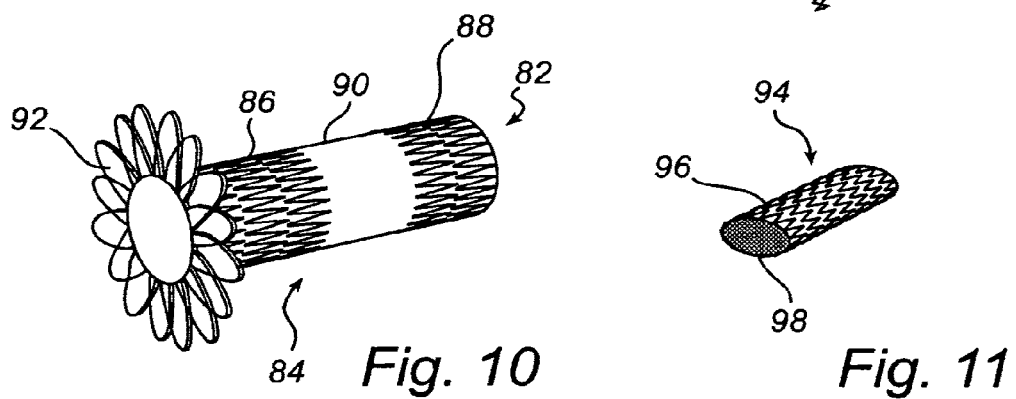

Referring now to FIG. 10, a fifth cutting device 82 adapted to be inserted into the RSPV is shown. This fifth cutting device 82 presents similar features as the second, third and fourth cutting devices 38, 54, 68. Thus, the fifth cutting device 82 also comprises a tubular part 84, which may consist of two or more tubular portions 86, 88, which are interconnected by a connecting member 90. The tubular part 84 of the fifth cutting device 82 presents similar features as the tubular part 40, 56, 70 of the second, third and fourth cutting devices 38, 54, 68. The fifth cutting device 82 also comprises an atrial end 92, similar to the atrial end 48, 64, 78 of the second, third and fourth cutting devices 38, 54, 68. However, the fifth cutting device 82 would normally not comprise any cutting arm, since it would normally be sufficient to penetrate the tissue around the RSPV. The fifth cutting device 82 may anyhow comprise a cutting arm adapted to extend towards any of the other PVs.

Referring now to FIG. 11, a sixth cutting device 94 adapted to be inserted into the left atrial appendage {LAA) or the right atrial appendage (RAA) is shown. The sixth cutting device 94 comprises a tubular part 96, which has an elliptic cross-section to fit into the elliptic form of the orifice of the LAA. A sixth cutting device 94 adapted to be inserted into the RAA will have a tubular part 96 with a less elliptic cross-section to fit the orifice of the RAA. The sixth cutting device 94 is adapted to be inserted into the orifice of the LAA inside the left atrium or into the orifice of the RAA inside the right atrium. The sixth cutting device 94 will further change shape by expanding its tubular part 96 through the atrial wall at the orifice. Thus, the LAA or the RAA will be completely cut off from electrical contact with the rest of the heart tissue. The tubular part 96 of the sixth cutting device 94 may be quite short extending from the orifice of the atrial appendage along its wall into the atrial appendage. Further, the tubular part 96 may be funnel-shaped, whereby a portion of the tubular part 96 may be designed to change shape in order to assume a cross-section that will not penetrate through the entire heart wall. This portion of the tubular part 96 may then serve to keep the sixth cutting device 94 in place. Further, another portion of the tubular part 96 will penetrate through the entire heart wall in order to effectively electrically isolate the atrial appendage from the rest of the heart. A sixth cutting device 94 adapted to be inserted into the LAA may comprise a cutting arm (not shown), which is adapted to change shape to penetrate through the heart tissue extending from the LAA to a fourth cutting device 68 inserted into the LSPV. Further, a sixth cutting device 94 adapted to be inserted into the LAA may comprise a film 98 covering an end of the tubular part 96 to be inserted closest to the orifice of the LAA. When the tubular part 96 is expanded into the heart wall, the film 98 will cover the orifice of the LAA, excluding the LAA from the blood circulating through the heart, whereby a dislocation of thrombus and clot formation in the LAA will be avoided.

Figures 12A, 12B:
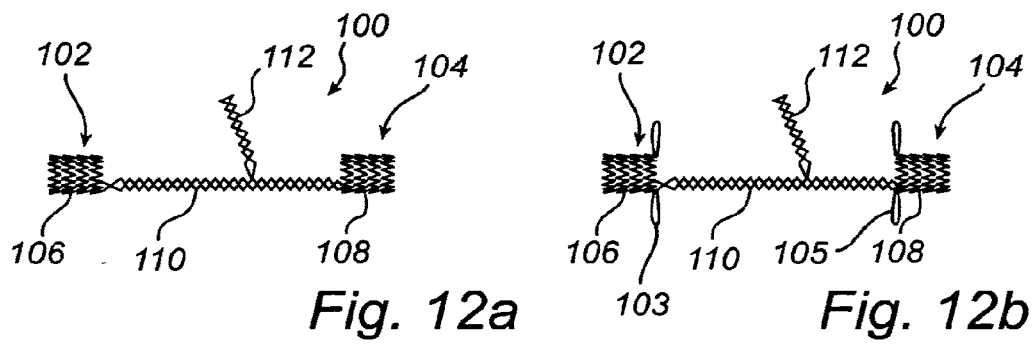

Referring now to FIG. 12*a*, a seventh cutting device 100 adapted to be inserted into the IVC and the SVC is shown. The seventh cutting device 100 comprises two pieces 102, 104, a first piece 102 to be inserted into the SVC and a second piece 104 to be inserted into the IVC. Each piece 102, 104 of the seventh cutting device 100 comprises a tubular part 106, 108, which presents similar features as the tubular part 40, 56, 70, 84 of the second, third, fourth, and fifth cutting devices 38, 54, 68, 82. Each tubular part 106, 108 may advantageously be funnel-shaped, wherein an end having the largest cross-section is adapted to be inserted closest to the orifice of the IVC or the SVC, respectively. The seventh cutting device 100 further comprises a connecting cutting arm 110. The seventh cutting device 100 is arranged to change shape such that this connecting cutting arm 110 will extend between the tubular part 106 of the first piece 102 inserted into the SVC and the tubular part 108 of the second piece 104 inserted into the IVC. This change of shape will cause the connecting cutting arm 110 to penetrate through the lateral right atrium heart wall tissue between the orifice of the SVC and the orifice of the IVC. The connecting cutting arm 110 may be attached to any one of the first and the second piece 102, 104 of the seventh cutting device 100, and preferably the connecting cutting arm 110 is attached to both the first and the second pieces 102, 104. If the connecting cutting arm 110 is only attached to one of the first and second pieces 102, 104, it will connect the first and the second pieces 102, 104 together after the change of shape has occurred. The connecting cutting arm 110 may comprise a branch 112, which, after the change of shape of the seventh cutting device 100, will extend from a point of the connecting cutting arm 110 laterally through the right atrial wall, whereby this branch 112 will penetrate the right lateral wall of the right atrium. As for the cutting arms, the branch 112 may be constructed of one loop or several sequential loops in a longitudinal direction of the branch 112. The seventh cutting device 100 may comprise a further cutting arm (not shown), which may be attached to the tubular part 108 of the second piece 104 that is inserted into the IVC. The seventh cutting device 100 is then arranged to change shape such that this further cutting arm will extend from the tubular part 108 of the second piece 104 inserted into the IVC towards and into the orifice of the CS. This change of shape will cause the further cutting arm to penetrate through the heart wall tissue between the orifice of the IVC and CS. This further cutting arm may alternatively be arranged as a further branch of the connecting cutting arm 110. The seventh cutting device 100 may, in a simple version for treating mild forms of disorders to the heart rhythm regulation system, consist of only the first piece 102 adapted to be inserted into the SVC, which first piece 102 may or may not comprise a cutting arm. As shown in FIG. 12b, the first and second pieces 102, 104 may also each comprise an atrial end 103, 105, similar to the atrial end 48, 64, 78, 92 of the second, third, fourth, and fifth cutting devices 38, 54, 68, 82.

Figure 13:
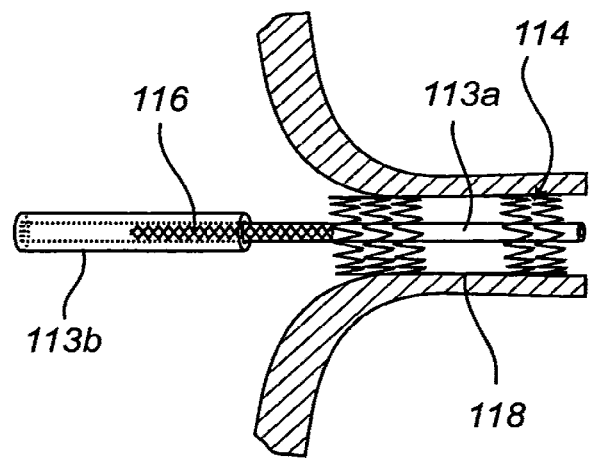
FIG. 13 shows a tissue lesion creating device comprising a cutting arm according to an embodiment of the invention, the tissue lesion creating device being shown inserted into a vessel with the cutting arm extending into a heart atrium before the tissue lesion creating device has started acting on the heart wall tissue.
Figure 14:
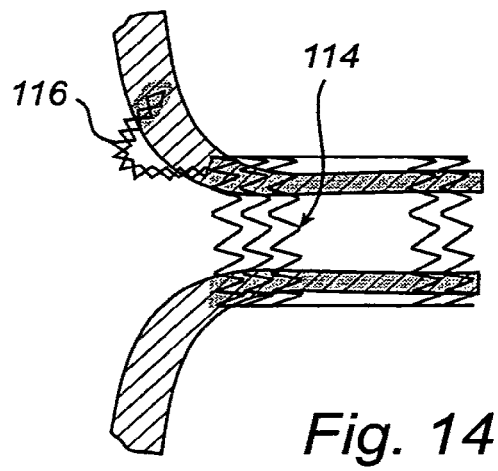
FIG. 14 shows the tissue lesion creating device of FIG. 13 during the time when the cutting arm penetrates a heart wall and the tissue lesion creating device penetrates tissue at the orifice of a vessel.
Figure 15A:
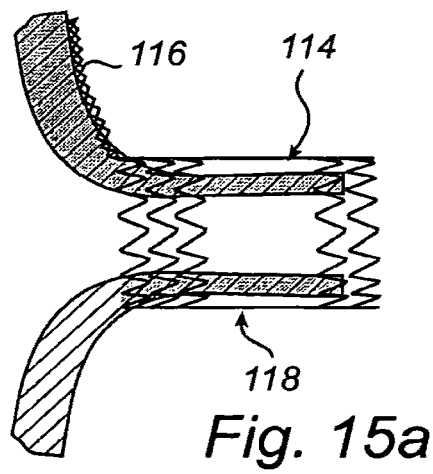
FIG. 15a shows the tissue lesion creating device of FIG. 13 after the tissue lesion creating device has penetrated the heart wall and the vessel wall at the orifice area and has completed a change of shape.
Figure 15B:
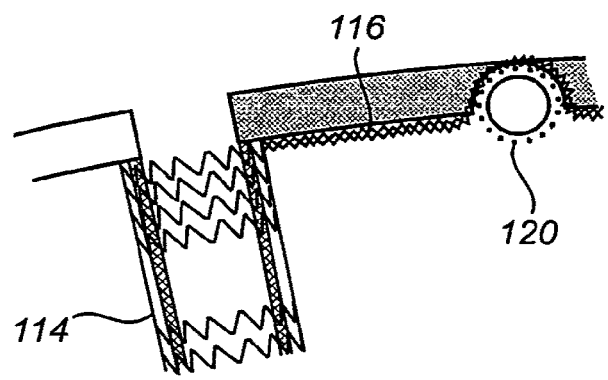
FIG. 15b shows the tissue lesion creating device of FIG. 13 after the device has penetrated the heart wall and has completed a change of shape similarly to FIG. 15a, but where the cutting arm of the device abuts another tissue lesion creating device inserted into another vessel.
Figure 15C:
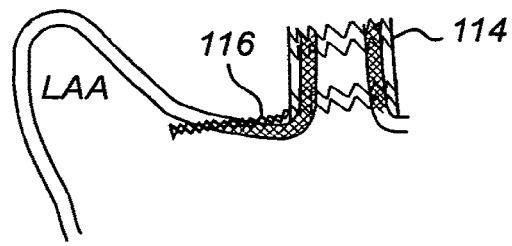
FIG. 15c is a schematic view showing the tissue lesion creating device of FIG. 13 after it has completed its change of shape, wherein the tissue lesion creating device has been inserted into the left superior pulmonary vein and the cutting arm is extended to the left atrial appendage opening.
Figure 15D:
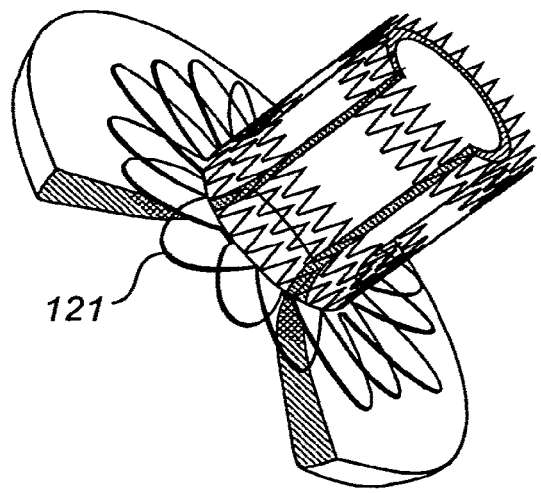
FIG. 15d is a perspective view with a section of the vessel and the heart wall cut-off and shows the tissue lesion creating device of FIG. 13 after the device has penetrated the heart wall and has completed a change of shape similarly to FIG. 15a, but where the tissue lesion creating device comprises an atrial end instead of the cutting arm.

Referring now to FIGS. 13-15, the action of a cutting arm will be explained in further detail. In FIG. 13, a cutting device 114 comprising a cutting arm 116 has been inserted into a blood vessel at the orifice of the opening into the heart. The cutting device 114 comprises a tubular part 118, which is inserted into the blood vessel. The cutting arm 116 is attached to the tubular part 118 and extends into the heart. In FIG. 13, the cutting device 114 is shown in an intermediate shape, which it has during insertion of the cutting device 114. The cutting device 114 has carried to the illustrated position on a catheter 113a while being restrained by a restraining sheath 113b. The cutting device 114 is shown when the tubular part 118 has been released while the cutting arm 114 is still restrained by the restraining sheath 113b. Thus, a change of shape has not yet been fully commenced. In FIG. 14, the cutting device 114 is shown during its action of changing its shape. Thus, the cutting arm 116 is extending from the inside of the heart into the heart wall tissue having penetrated heart tissue during the shape-change. The cutting arm 116 will continue penetrating heart tissue in order to obtain the permanent shape of the cutting device 114. In FIG. 15a, the cutting device 114 is shown after having completed its change of shape. The tubular part 118 has now cut through the vessel wall and penetrated heart tissue around the vessel. Further, the cutting arm 116 is now completely outside the heart. Thus, the cutting arm 116 has now penetrated the entire heart wall and has therefore caused a lesion along a cutting line from the orifice of the blood vessel wall through the selected adjacent heart wall. The penetrated tissue is marked with shading in FIG. 15a, as well as in FIGS. 15b-d. In FIG. 15b, the cutting arm 116 of the cutting device 114 is shown abutting another cutting device 120, which has been inserted into another blood vessel. In this way, the cutting arm 116 has performed a lesion between the two cutting devices, whereby an effective block against propagation of undesired electrical signals has been created. The position of the cutting arm 116 is also stabilized after the change of shape by the cutting arm 116 resting on the other cutting device 120. In, FIG. 15c, the cutting device 114 is shown inserted into the LSPV, and the cutting arm 116 has been extended leaning into the orifice of the LAA and thereby penetrating the atrial wall between the LAA and the LSPV. In addition to the cutting of the cutting arm 116, the tubular part 118 of the cutting device 114 inserted inside the vessel has treated the vessel wall adjacent to the orifice, which often contains ectopic sites. In FIG. 15d, the cutting device 114 is shown comprising an atrial end 121, which has penetrated the tissue around the orifice of the blood vessel.

Referring now to FIGS. 16-26, there is shown cutting patterns being obtained in a few different embodiments, illustrating a few examples of sets of cutting devices being inserted into blood vessels adjacent the heart and the treatment obtained by these sets of cutting devices. The treatment needed may differ from patient to patient and other patterns may be conceivable using the concept of inserting cutting devices into blood vessels adjacent the heart.

Figure 16:
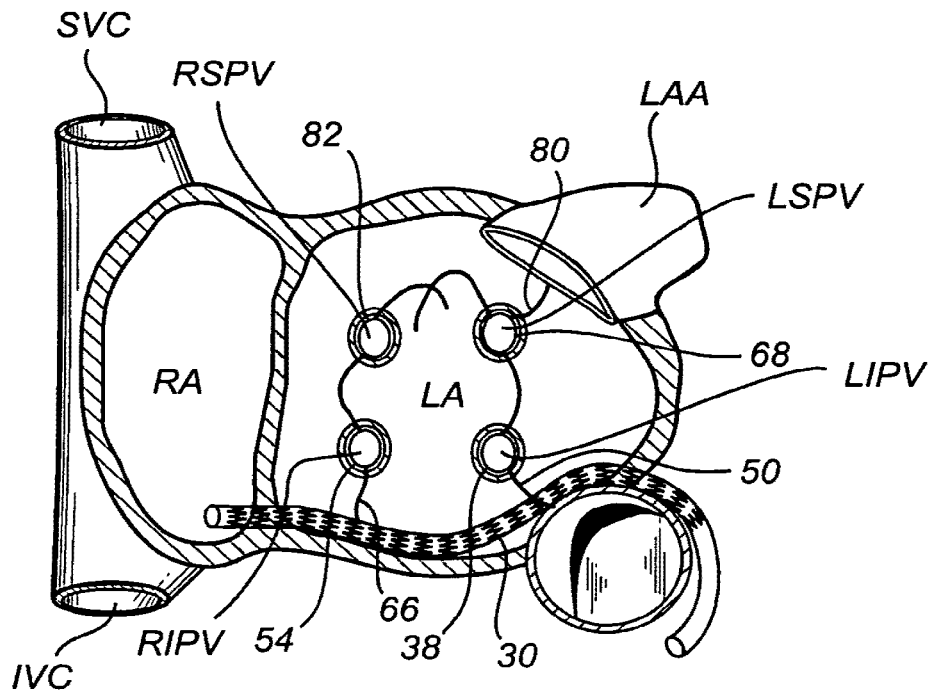

In FIG. 16, the first, second, third, fourth and fifth cutting devices 30, 38, 54, 68, 82 having been inserted into the four PVs are shown. The cutting devices 30, 38, 54,68, 82 are shown in an intermediate shape, which they present shortly after having been delivered to the desired positions and before any penetration of heart wall tissue has begun. The tubular parts 40, 56, 70, 84 of the second, third, fourth and fifth cutting devices 38, 54, 68, 82 have expanded to abut the wall of its respective PV. The cutting arms of the second, third, fourth and fifth cutting devices 38, 54, 68, 82 have been diverted from the axial direction of the tubular part to abut the inside of left atrial wall of the heart. The second cutting device 38 inserted into the LIPV is shown having a cutting arm 50 extending to the mitral valve. The third cutting device 54 inserted into the RIPV has a cutting arm 66 extending to the CS. Thus, instead of forming the cuts 12 and 14 according to FIG. 3, cuts are formed from the LIPV and the RIPV to the CS. These cuts 12 and 14 are very difficult to accomplish using the technique of inserting cutting devices into the blood vessels. However, these cuts may be replaced by the more easily accomplished cutting pattern formed by the arms 50 and 66 in combination with a cut formed by the first device 30 inserted into the CS when expanded out of the CS. Thus, with the arms 50 and 66 in direct contact with the first cutting device 30 inserted in the CS, the same effect as from the cuts 12 and 14 in FIG. 3 is achieved. The second cutting device 38 inserted into the LIPV is further shown having a cutting arm extending to the LSPV. The third cutting device 54 inserted into the RIPV is further shown having a cutting arm extending to the RSPV. The fourth cutting device 68 inserted into the LSPV is shown having a cutting arm 80 extending to the LAA. The fifth cutting device 82 inserted into the RSPV is shown having a cutting arm extending to the fourth cutting device 68. The cutting arms of the cutting devices 38, 54, 68, 82 may be arranged in any desired combination between the cutting devices 38, 54, 68, 82 forming connections between the cutting devices 38, 54, 68, 82. However, the cutting arms may also be arranged freely, without necessarily having contact to another cutting device.

Figure 17:
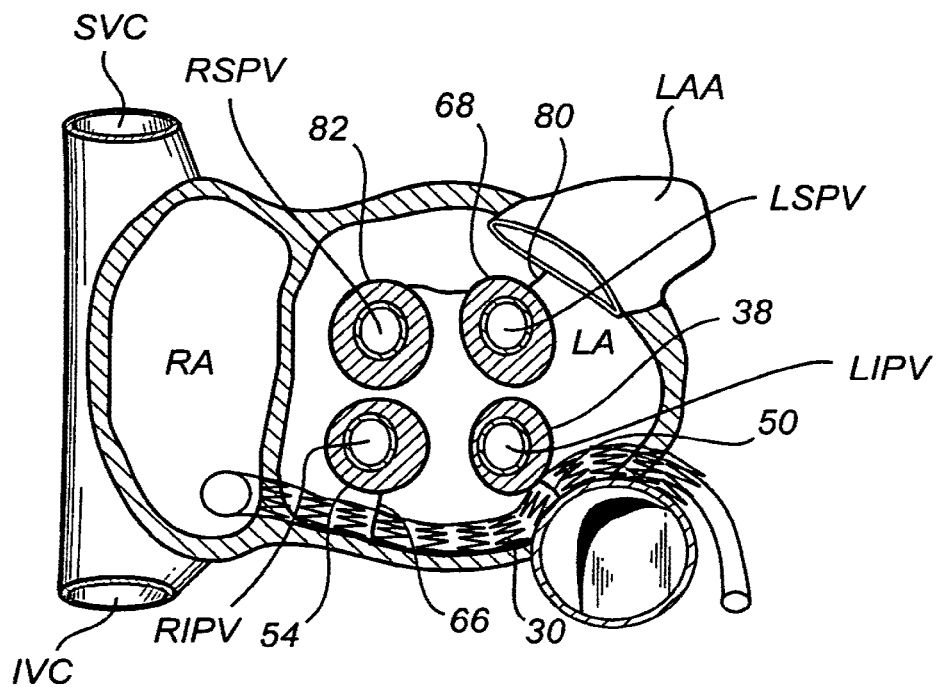

In FIG. 17, the cutting devices shown in FIG. 16 are shown after the change of shape of the devices has occurred. Now, the second, third, fourth and fifth cutting devices 38, 54, 68, 82 have expanded out of the respective PVs and the treated tissue around the orifices of the PVs is shown in shading. Further, the cutting arms have penetrated the heart tissue and have created cutting lines between the PVs, from the LIPV to the mitral valve, from the LSPV to the CS, and from the LSPV to the LAA orifice.

Figure 18:
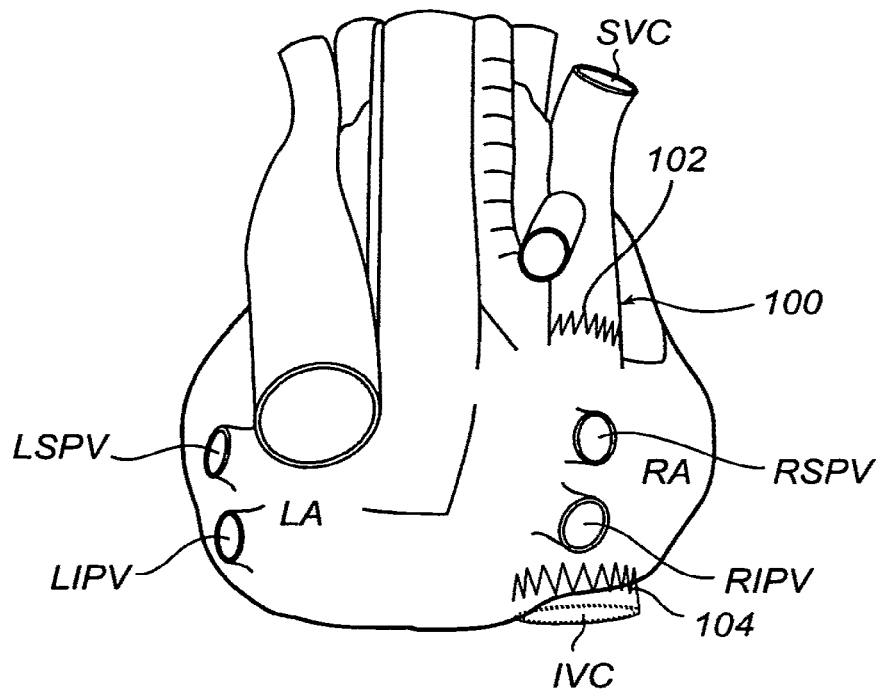
Figure 19:
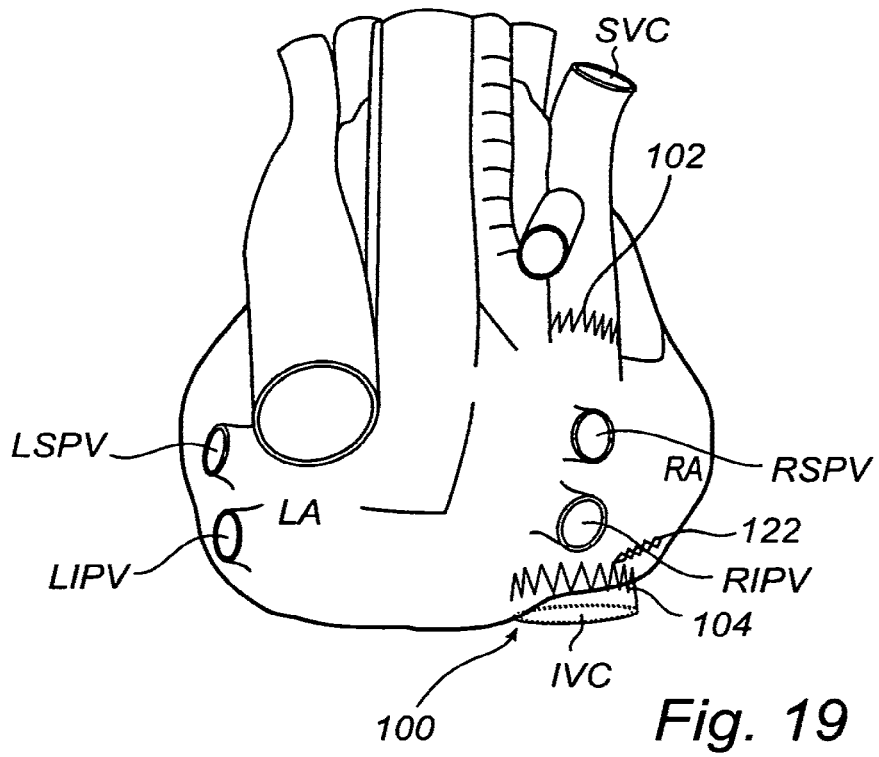
Figure 20:
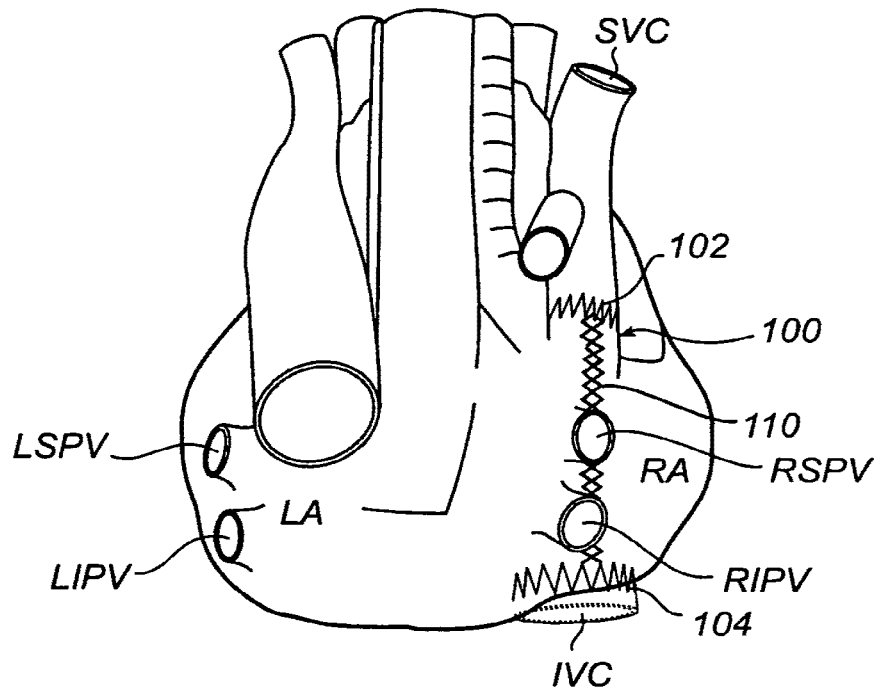
Figure 21:
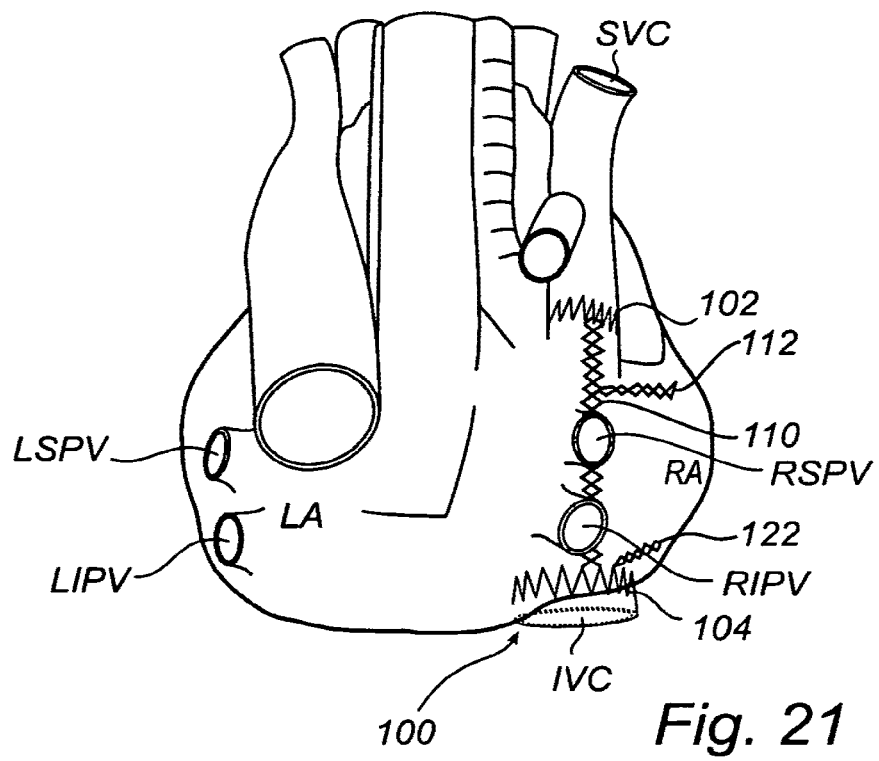

In FIGS. 18-21, different embodiments of the seventh cutting device 100 inserted into the SVC and the IVC is shown. In FIG. 18, the first and second pieces 102, 104 of the seventh cutting device 100 are shown being inserted at the orifices of the SVC and the IVC. The first and second pieces 102, 104 will treat the heart tissue around the orifices of the SVC and the IVC, respectively. In FIG. 19, the second piece 104 is shown comprising a cutting arm 122, which extends from the orifice of the IVC into the orifice of the CS, whereby the cutting arm 122 penetrates heart tissue of the right atrium free wall. In FIG. 20, the seventh cutting device 100 is shown comprising the connecting cutting arm 110, which extends between the first piece 102 inserted into the SVC and the second piece 104 inserted into the IVC. The connecting cutting arm 110 will penetrate heart tissue in the right lateral aspect and the right lateral to posterior aspect of the right atrial wall. In FIG. 21, the seventh cutting device 100 is shown comprising a branch 112 of the connecting cutting arm 110. The branch 112 extends from a point on the connecting cutting arm 110 laterally, creating a vertical cut outwards in the lateral right atrium wall. Alternatively, this branch 112 may be arranged as a further cutting arm extending from the first piece 102 inserted into the SVC.

Figure 22:
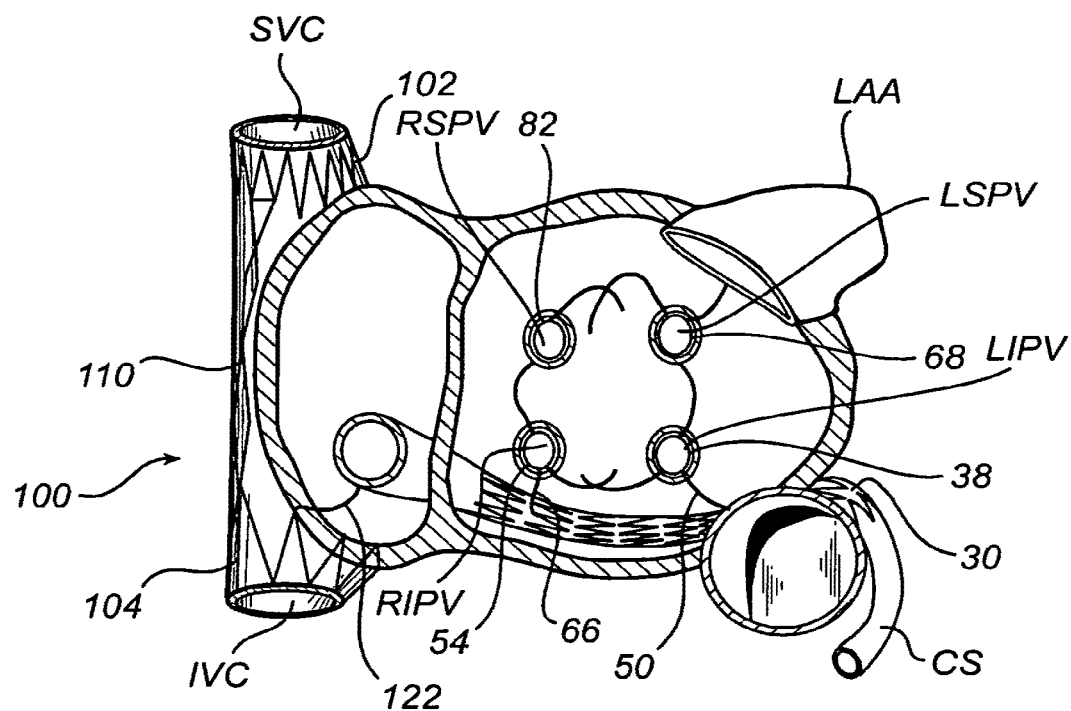
Figure 23:
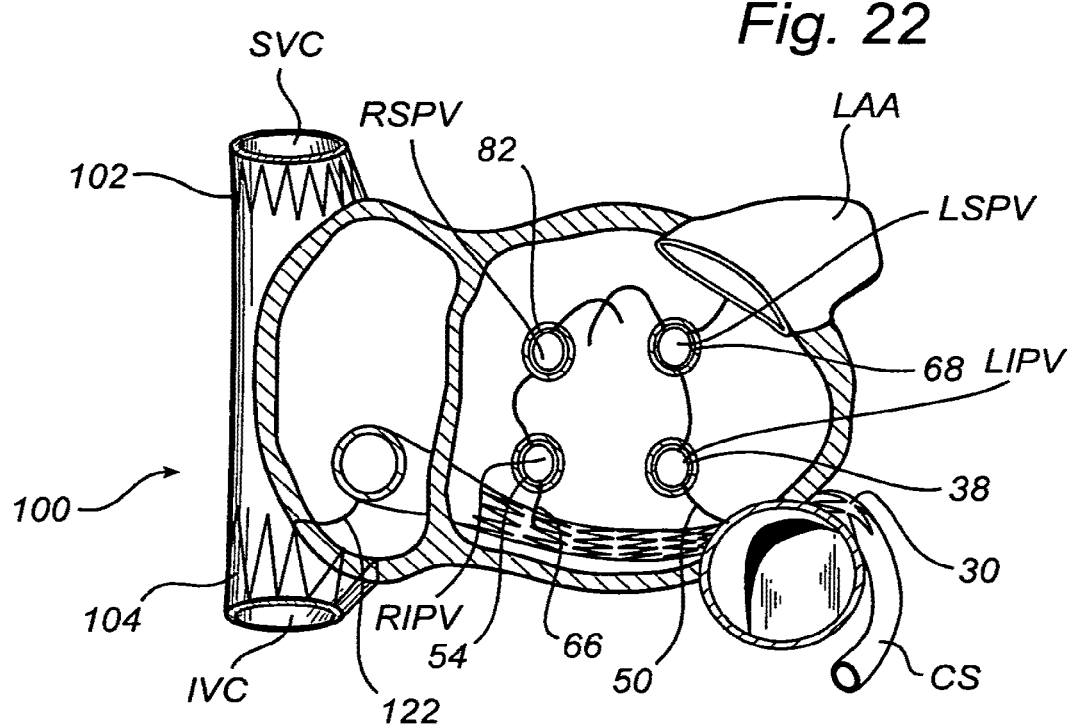

In FIGS. 22-23, the first, second, third, fourth, fifth, and seventh cutting devices 30, 38, 54, 68, 82, 100 are shown inserted into the CS, the PVs and the IVC and the SVC, respectively. The cutting devices are shown in an intermediate state corresponding to the state shown in FIG. 16. Both FIGS. 22 and 23 illustrate cutting arms between the PVs and from the LIPV past the first cutting device 30 in the CS extending to the mitral valve. Thus, the first cutting device 30 inserted in the CS provides a support for the cutting arms extending from the PVs for stabilizing the position of the cutting arms after the change of shape of the cutting devices has been completed. The first cutting device 30 inserted into the CS has, at least partly, an elliptic cross-section enabling the first cutting device 30 to penetrate tissue close to the mitral valve. Also, there is a cutting arm 122 extending from the IVC to the orifice of the CS. In FIG. 22, there is shown the connecting cutting arm 110 between the SVC and the IVC, whereas this connecting cutting arm is not present in FIG. 23. The cutting patterns shown in FIGS. 22 and 23 illustrate cutting patterns that will effectively block propagation of undesired electrical signals in the heart tissue for most patients suffering from disorders to the heart rhythm regulation system. Thus, inserting cutting devices to create these cutting patterns may effectively treat most patients suffering from disorders to the heart rhythm regulation system. However, these cutting patterns do not illustrate treatment of the atrial appendages, as will be shown in FIGS. 24-26. It should be appreciated that the cutting pattern of FIGS. 22 and 23 may be supplemented with this treatment of the atrial appendages.

Figure 24A:
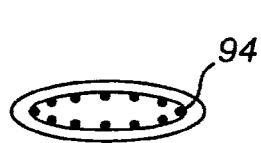
Figure 24B:
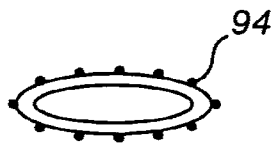
Figure 25:
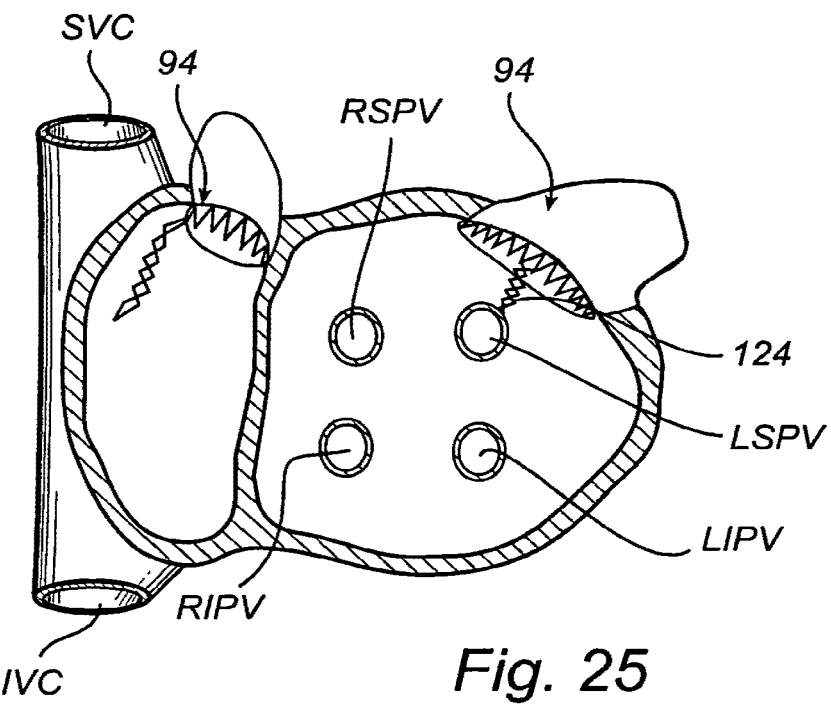
FIGS. 25-26 illustrate tissue lesion creating devices inserted into the left atrial appendage and the right atrial appendage, the figures showing a cross-section that has been cut through the atria of the heart.
Figure 26:
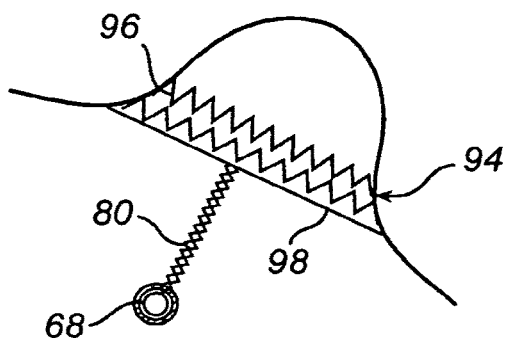

In FIGS. 24-26, there is shown the sixth cutting devices 94 inserted into the LAA and the RAA. As shown in FIGS. 24a-b in cross-section, the sixth cutting device 94 is inserted at the orifice of the appendage (FIG. 24a) and expanded at this position to penetrate through the heart wall (FIG. 24b). The sixth cutting device 94 has an elliptic cross-section to fit to the shape of the appendage. In FIG. 25, sixth cutting devices 94 are shown inserted into the LAA and the RAA. The sixth cutting device 94 inserted into the LAA is shown having a cutting arm 124 extending to the LSPV, and the sixth cutting device 94 inserted into the RAA is shown having a cutting arm extending along the lateral right atrium wall. In FIG. 26, the sixth cutting device 94 is shown inserted into the LAA. This sixth cutting 94 device has no cutting arm; instead a fourth cutting device 68 inserted into the LSPV is shown having a cutting arm 80 extending to the LAA. The sixth cutting device 94 inserted into the LAA has a film or membrane 98 covering an end of its tubular part 96 at the LAA orifice. This film or membrane 98 will exclude the LAA from blood contact with the rest of the heart and thereby prohibit migration of thrombus or clot formation from the LAA to, for instance, the brain.

Now, a system for delivery of a cutting device into a desired position in a blood vessel adjacent the heart will be described. Each cutting device may be inserted into its desired position using such a delivery system. The delivery system allows a precise placement of each cutting device into the heart and the big vessels of the body. The delivery system has a restraining device, which keeps the cutting device in its temporary shape. This allows insertion into the blood vessel through catheters having a small bore, making minimal trauma to the patient. The restraining device may be a restraining tube, into which the cutting device is forced in its temporary shape. By cooling the cutting device, in case of a cutting device made of Nitinol, it may be easier to force the cutting device into the restraining tube. Once inserted into the, desired position, the cutting device may be pushed out of the restraining tube by means of a piston or the cutting device may be released by retracting the restraining tube from its position over the cutting device. In case of a cutting device made of Nitinol, the cutting device may also be restrained by cooling to prevent it from obtaining a transition temperature trigging the change of shape. Thus, the cutting device may be restrained by cooling during insertion into the desired position and released by suspension of the cooling when inserted at the desired position. In WO 03/022179, such a delivery system is described in more detail.

Now, a method for treating a patient having a disorder to the heart rhythm regulation system will be described. The patient is prepared for operation and operation is performed in an environment allowing visualization of the heart and the attached big vessels using fluoroscopy and ultrasound according to conventional techniques.

Figure 27:
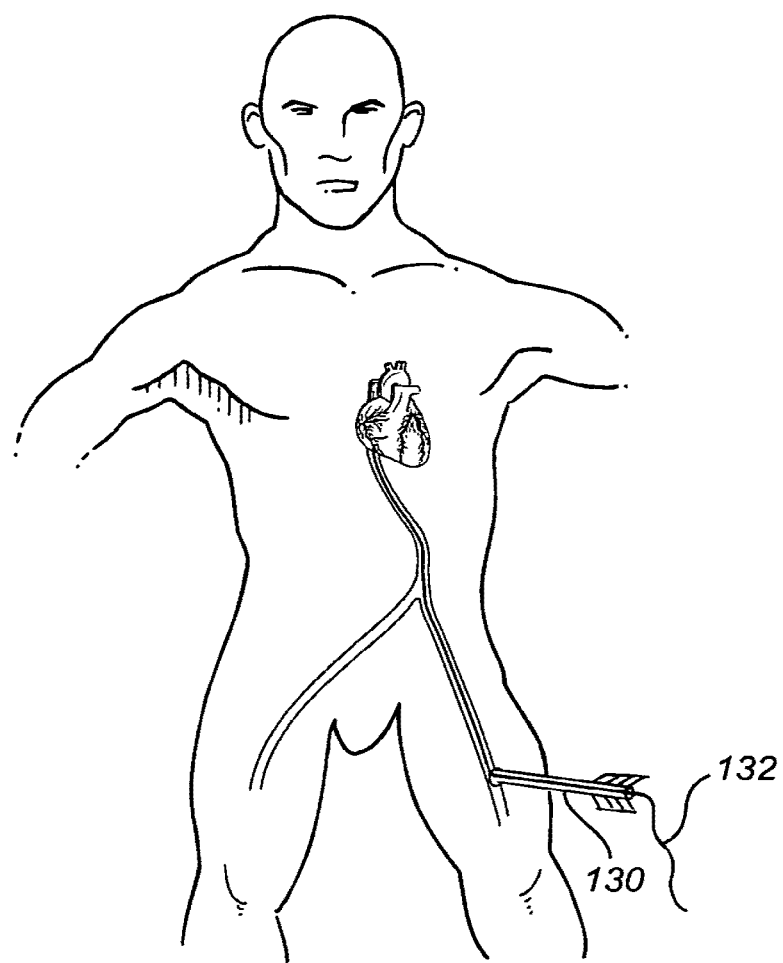
FIGS. 27-29 illustrate three different embodiments of accessing the vascular system.
Figure 28:
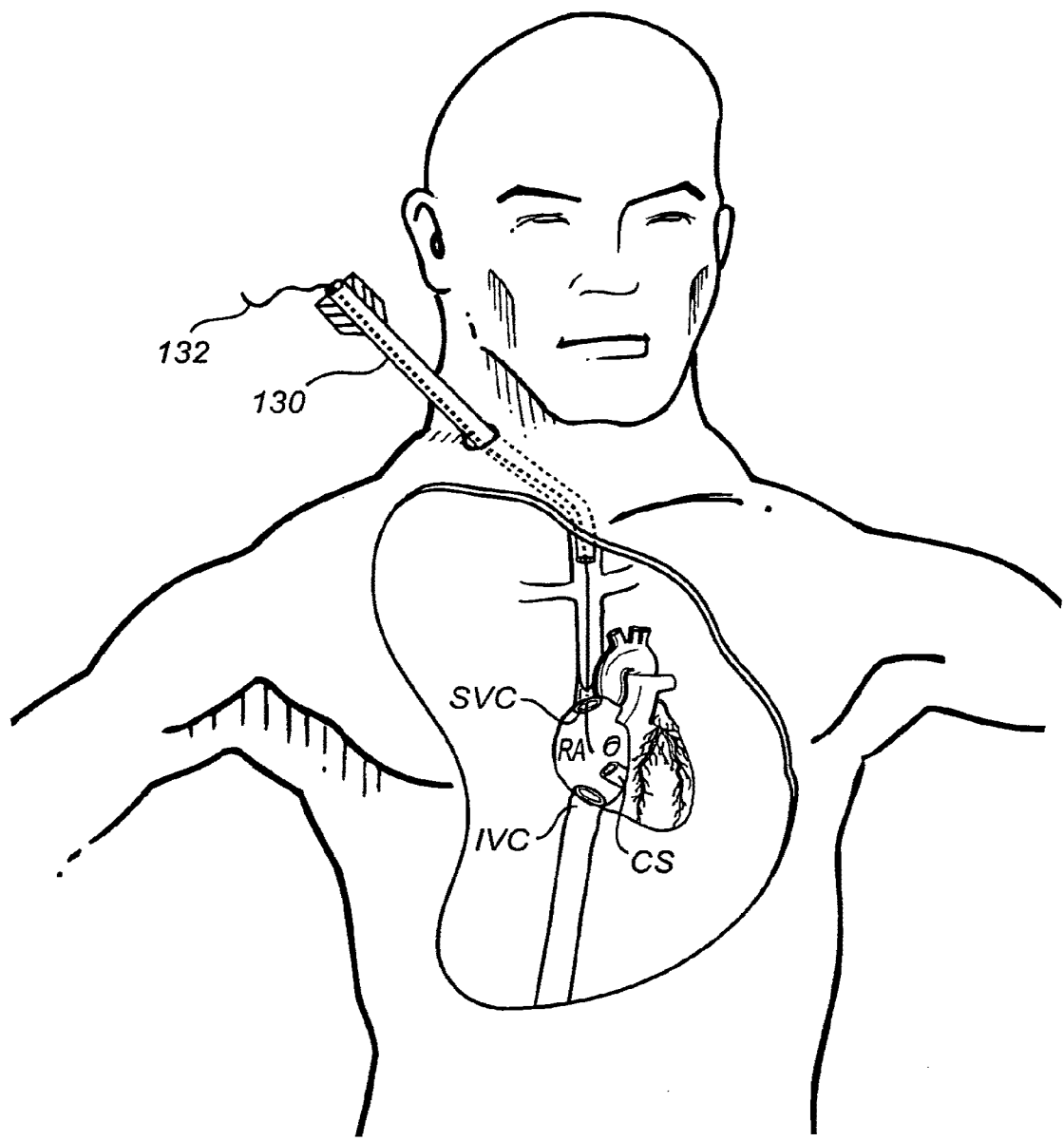
Figure 29:
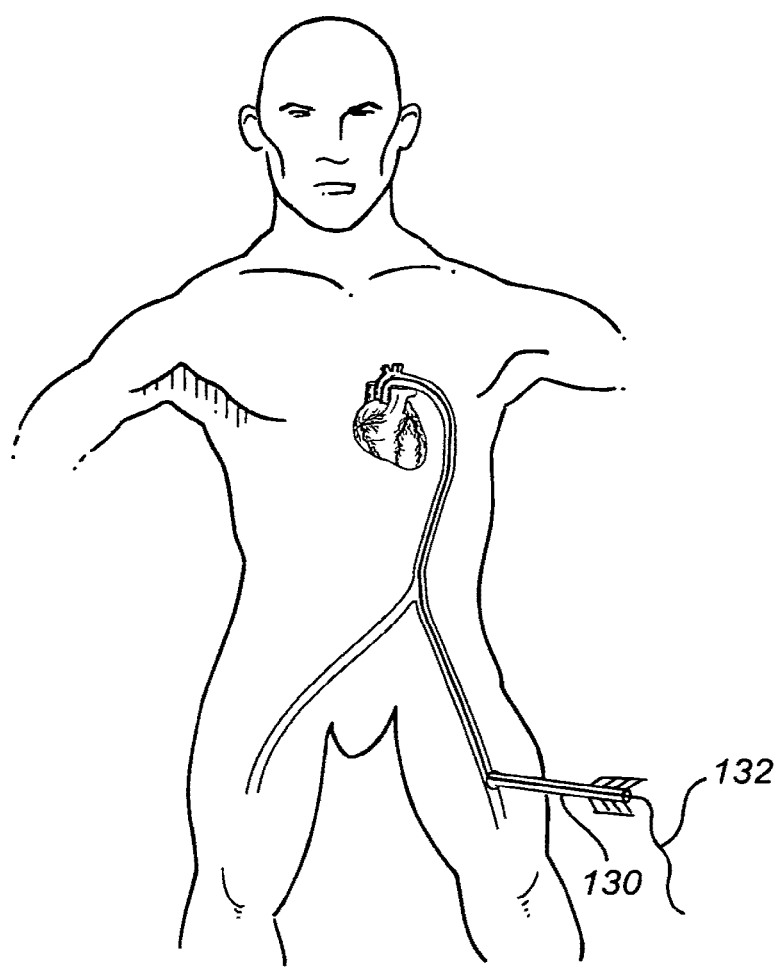
Figure 30:
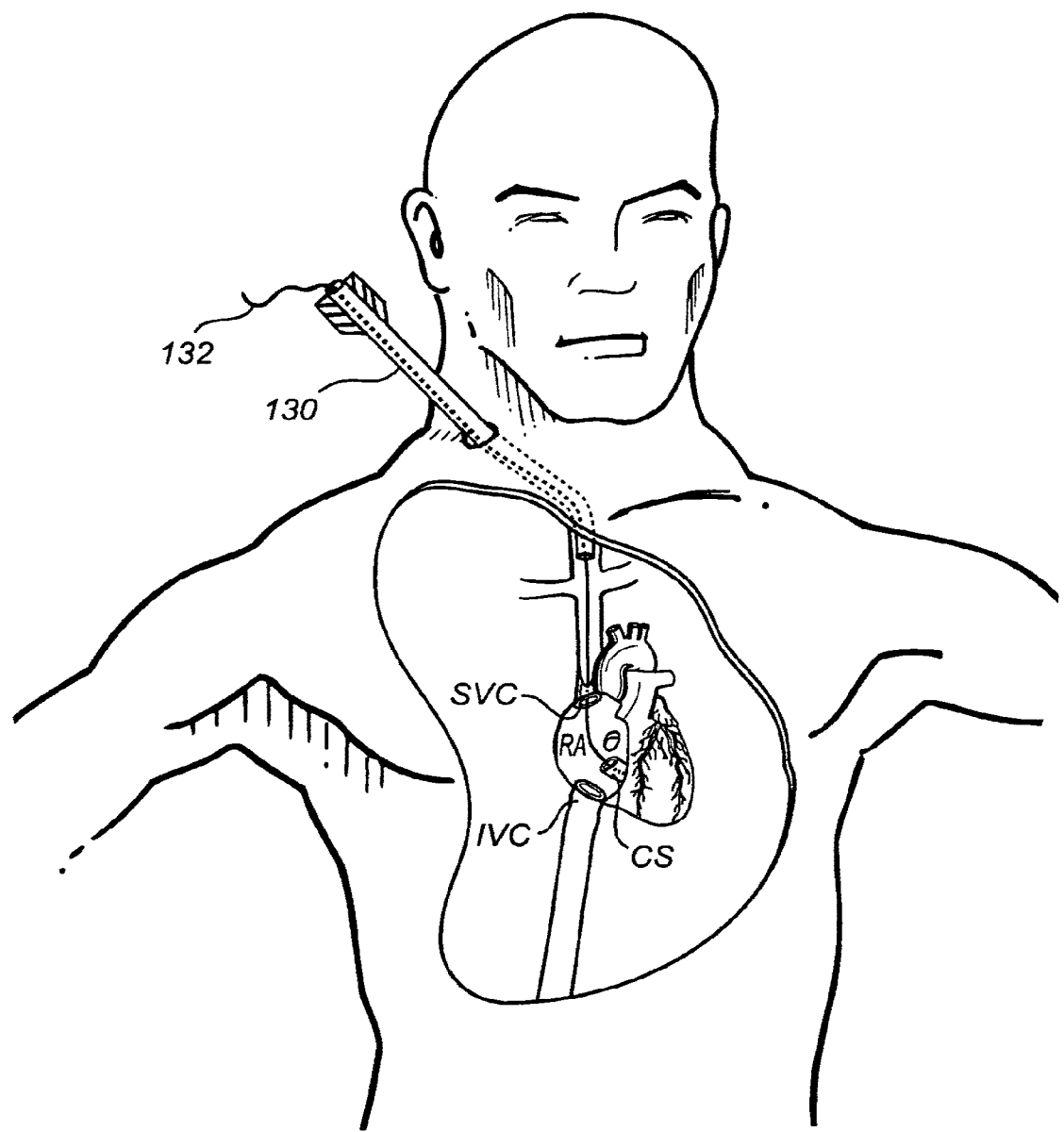
FIG. 30 illustrates a guide wire being inserted into the coronary sinus.

The operation is started by making a puncture of a vein providing an access point to the vascular system of the patient according to conventional techniques. Usually, the femoral vein in the groin, as illustrated in FIG. 27, the subclavian vein on the chest, or the internal or external jugular vein on the neck, as illustrated in FIG. 28, is used. However, other smaller veins may be used instead. Also, in difficult cases when the pulmonary veins cannot be accessed from the vein, arterial access through the femoral artery in the groin may be used, as illustrated in FIG. 29. This method will, however, not be further discussed here. A delivery system is used for inserting the above described cutting devices into blood vessels adjacent the heart. First, an introducer sheath 130 of the delivery system is inserted at the puncture providing an access route into the vascular system. Then, a diagnostic catheter of the delivery system is inserted through the introducer sheath 130 into the vascular system. The diagnostic catheter is manoeuvred through the vascular system into the CS. Next, a guide wire 132 of the delivery system is inserted through a channel of the diagnostic catheter into the CS and all the way to the vein parallel to the left anterior descending artery of the heart, close to the apex of the heart. The guide wire 132 is inserted as far as possible into the vascular system to be firmly positioned. Thereafter, the diagnostic catheter is withdrawn from the patient. The guide wire 132 will then extend from outside the patient into the patient via the access point and inside the patient to the CS, as illustrated in FIG. 30.

Figure 31:
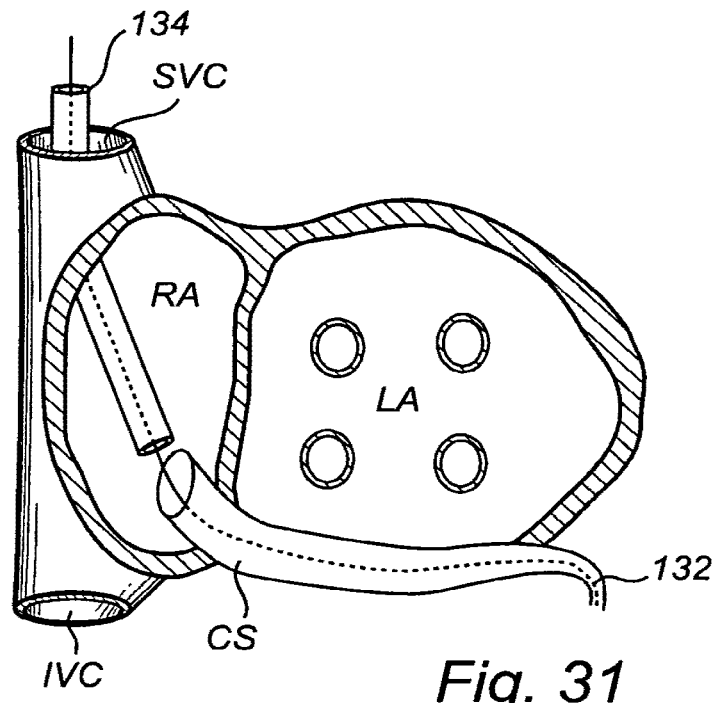
FIG. 31 illustrates a guide wire being inserted into the coronary sinus and a guide catheter being inserted with its tip at the orifice of the coronary sinus.

A guide catheter 134 of the delivery system is now inserted over the guide wire 132 so that the guide catheter 134 is positioned with its tip at the orifice of the CS, as illustrated in FIG. 31. Now, there is a guide wire 132 extending from the outside of the patient and the guide catheter 134, through the guide catheter 134, through the CS, the great cardiac vein and the anterior vein parallel to the LAD all the way to the apex of the heart.

Figure 32:
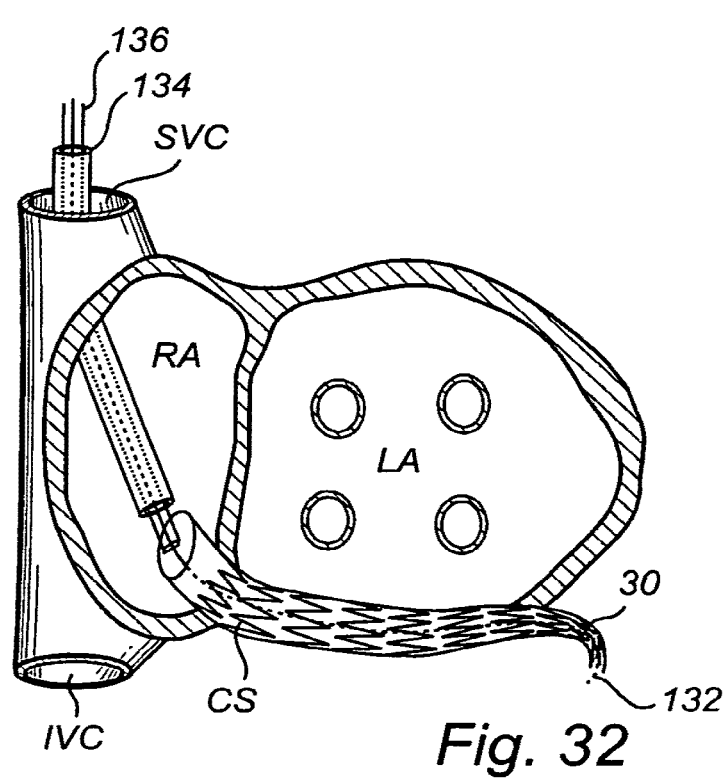
FIG. 32 is a view similar to FIG. 31 showing a first tissue lesion creating device being inserted into the coronary sinus.

Referring to FIG. 32, a delivery catheter 136 of the delivery system for carrying the first cutting device 30 into the desired position has a guide wire channel throughout its length. The end of the guide wire 132 outside the patient is then inserted into the guide wire channel of the delivery catheter 136, whereby the delivery catheter 136 may be inserted over the guide wire 132 and inside the guide catheter 134 into the CS. The delivery catheter 136 has an inner part providing the guide wire channel and carrying the cutting device at a distal portion. The delivery catheter 136 may further comprise an outer, restraining part, which covers the cutting device and keeps it in a contracted, temporary state. The restraining part may be axially displaceable in relation to the inner part. Thus, the restraining part may be retracted for releasing the cutting device. In this way, the first cutting device 30 is inserted into the CS and may be located in its desired position. A correct position is when the distal end 34 of the first cutting device 30 is positioned within the CS beyond the LIPV next to the CS and the proximal end 36 of the first cutting device 30 is closer to the orifice of the CS than the RIPV. Preferably, the first cutting device 30 extends all the way to the orifice of the CS. Without moving the first cutting device 30 away from its correct position, the first cutting device 30 is released from the delivery catheter. The first cutting device 30 will then immediately expand radially until contact is established with the CS wall, as illustrated in FIG. 32. Thereafter, the delivery catheter 136 is withdrawn from the patient.

However, the first cutting device 30 is arranged to change shape to assume a shape having much larger diameter than the natural diameter of the CS. Thus, the first cutting device 30 will expand to its designed, permanent shape and the CS wall will not be able to prevent the first cutting device 30 from obtaining its permanent shape. In order to obtain its permanent shape, the first cutting device 30 will therefore penetrate tissue in the path of the change of shape. In this way, the first cutting device 30 will expand to penetrate the heart tissue outside the CS, for instance the left atrium wall. The penetrated tissue will be killed and replaced by fibrous tissue, which is not able to transmit electrical signals. Thus, a block against propagation of undesired electrical signals may be created in this manner.

As an option, the first cutting device 30 may be inserted into the CS in a first separate session of the treatment of a patient. Thus, this first cutting device 30 may be allowed to be well-anchored in the tissue around the CS, before other cutting devices are inserted. This is suitable since some of the other cutting devices are adapted to contact the first cutting device 30 inserted into the CS in order to stabilize and fix their positions. The first cutting device 30 will be well-anchored within a few weeks, typically within three weeks. In this time the first cutting device 30 has penetrated the tissue around the CS and is firmly embedded by the tissue fixing its position. Then, the patient will come back for a second session of the treatment. Thus, a puncture is again made into a vein for allowing access again to the vascular system. However, all the cutting devices may alternatively be inserted during one session.

Figure 33:
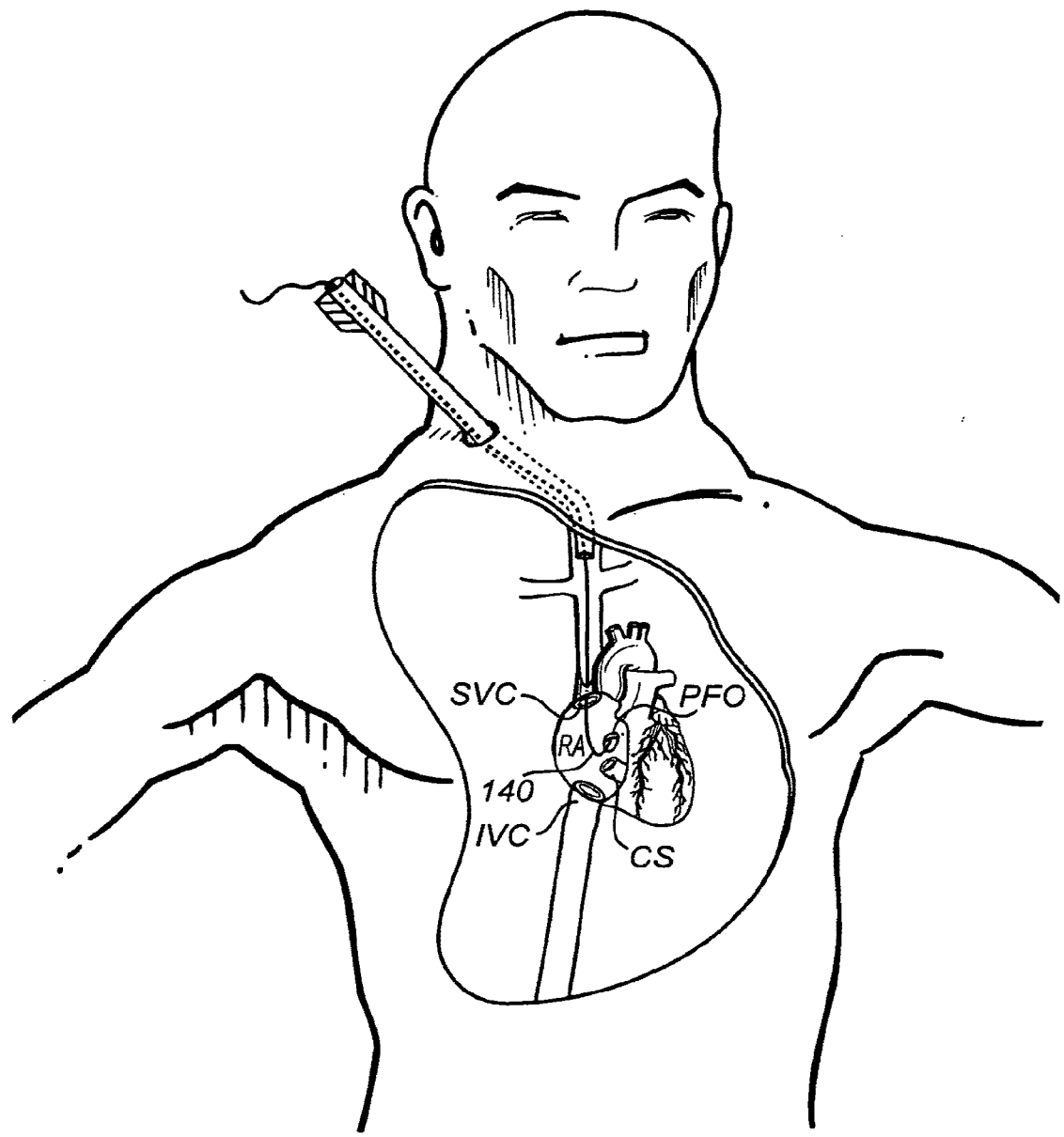
FIGS. 33 and 34 illustrate a guide wire having been inserted into the left atrium.
Figure 34:
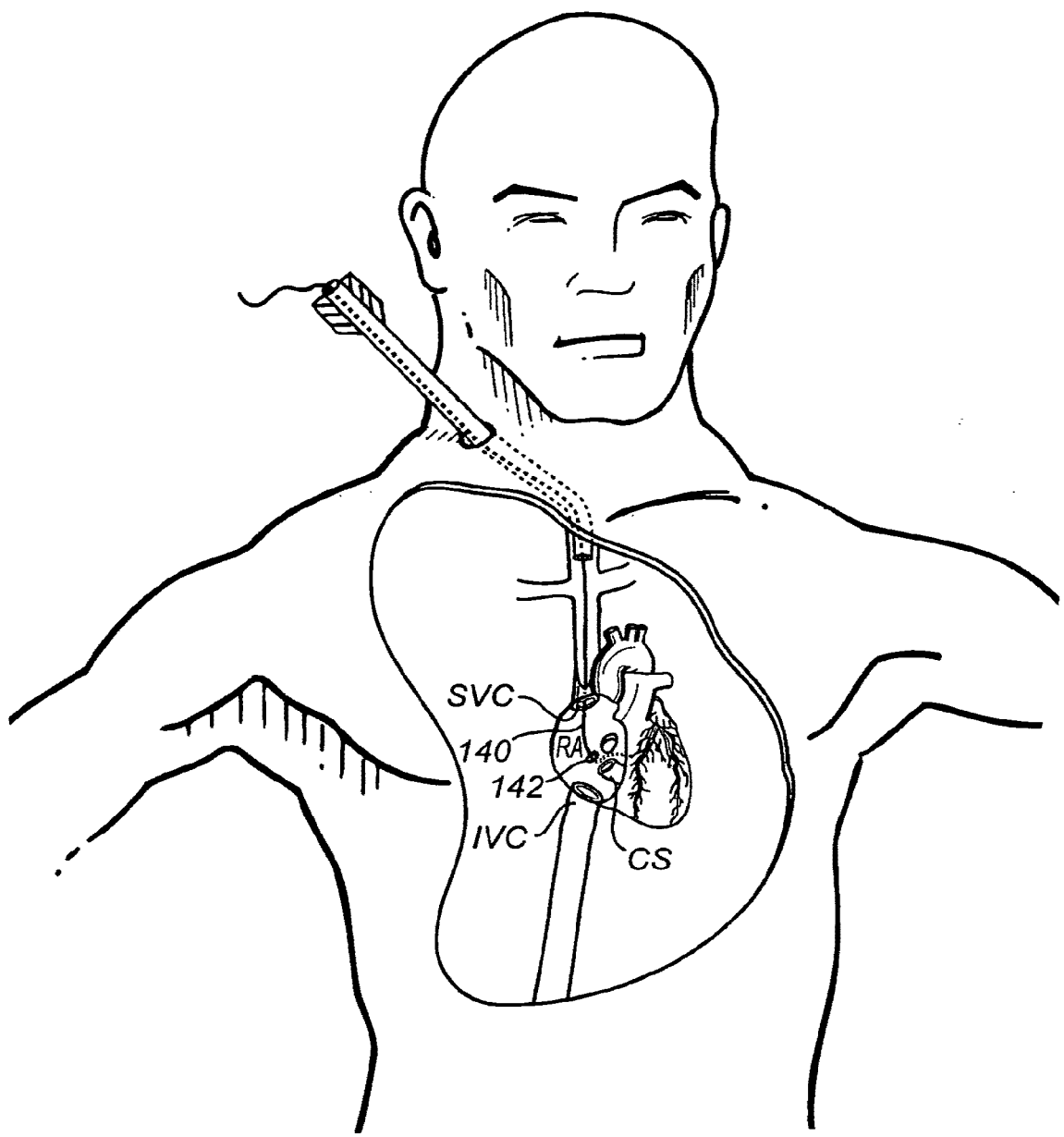

Now, a guide wire 140 is advanced inside a diagnostic catheter into the left atrium (LA), as illustrated in FIGS. 33 and 34. In order to access the LA, the atrial septum between the LA and the right atrium (RA) must be penetrated. If the patient has a patent foramen ovale {PFO, FIG. 33), which is an opening between the LA and the RA that is normally only present during the fetal period in humans, this may be used and enlarged, for instance by means of a balloon catheter (not shown). If no PFO is present (FIG. 34), a small opening 142 must first be created by means of a long flexible needle passed through a diagnostic catheter inside the access vein. Again, the opening 142 in the atrial septum may be enlarged by means of a balloon. Once the needle is inside the LA, the catheter is passed over the needle into the LA and the needle is retracted. A guide wire 140 may now be advanced through the catheter into the LA and further into the LIPV.

Figure 35:
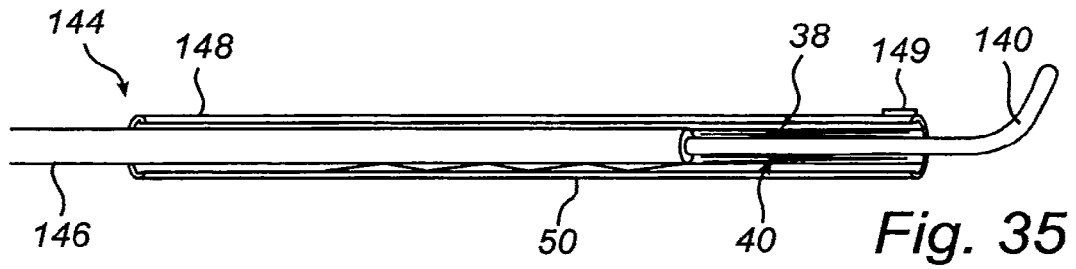
FIGS. 35-37 illustrate the carrying and deployment of a tissue lesion creating device by means of a delivery catheter.
Figure 36:
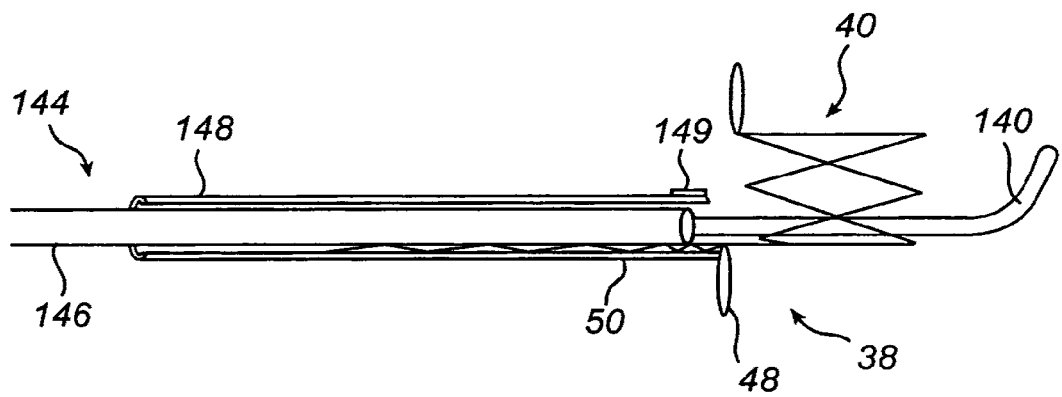
Figure 37:
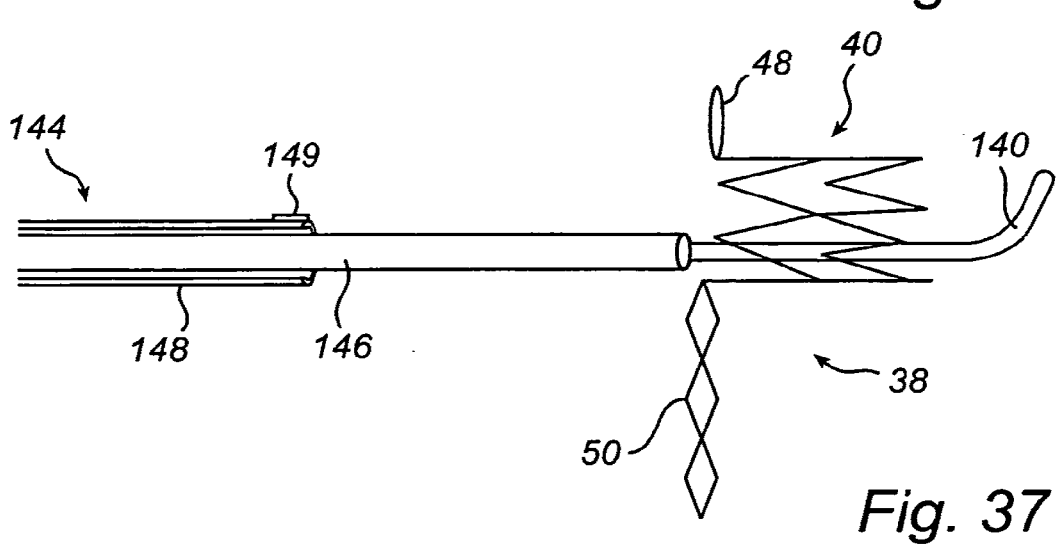

Referring now to FIGS. 35-37, the release of a cutting device will be generally described. Thus, having now placed the guide wire 140, the second cutting device 38 may be inserted to its desired position using a guide catheter extending to the LIPV orifice and a delivery catheter 144, as illustrated in FIG. 35, in a similar manner as for the insertion of the first cutting device 30. The delivery catheter 144 has an inner part 146 providing the guide wire channel. The tubular part 40 of the second cutting device 38 is arranged in front of the inner part 146 such that the inner part 146 of the delivery catheter 144 pushes the tubular part 40 in front of it. The delivery catheter 144 may further comprise an outer, restraining part 148, which covers the cutting device and keeps it in a contracted, temporary state. The restraining part 148 may be axially displaceable in relation to the inner part 146. Thus, the restraining part 148 may be retracted for releasing the cutting device 38. The delivery catheter 144 has a marker on the catheter outside the patient, as well as a x-ray marker 149 visible on the fluoroscopy, indicating securely the orientation of the cutting arm 50 of the second cutting device 38. The second cutting device 38 is now rotated into a position where it will change shape in such a way that the cutting arm 50 will extend to contact and be supported by the first cutting device 30, which has been inserted previously. The second cutting device 38 is advanced into a position where the atrial end 48 of the second cutting device 38 is still outside the LIPV orifice. When the correct position of the second cutting device 38 is confirmed by means of fluoroscopy and/or ultrasound, the distal end of the second cutting device 38 is released from the delivery catheter far inside the PV, whereby the distal end will expand radially to fix the position of the second cutting device 38. Next, a mid portion of the second cutting device 38 and the atrial end 48 is released, as illustrated in FIG. 36. Now, the cutting arm 50 is released, as illustrated in FIG. 37, and allowed to assume its radial extension from the tubular part 40, whereby it will penetrate the heart wall to contact the first cutting device 30.

Now, the guide wire 140 is retracted into the LA. The diagnostic catheter is inserted again and guided into the RIPV, whereby the guide wire 140 may be inserted into the RIPV. Thereafter, the diagnostic catheter is withdrawn from the patient. Then, the third cutting device 54 is inserted using a guide catheter extending to the RIPV orifice and a delivery catheter 144 in a manner similar to the insertion of the second cutting device 38. Thus, the orientation of the cutting arm 66 of the third cutting device 54 is determined in the same manner as for the second cutting device 38. Having correctly positioned the third cutting device 54, the tubular part 56, the atrial end 64 and the cutting arm 66 of the third cutting device 54 are released in a manner similar to the release of the second cutting device 38. Now, the cutting arm 66 is released and allowed to assume its radial extension from the tubular part 56, whereby it will penetrate the heart wall to contact the first cutting device 30.

Figure 38:
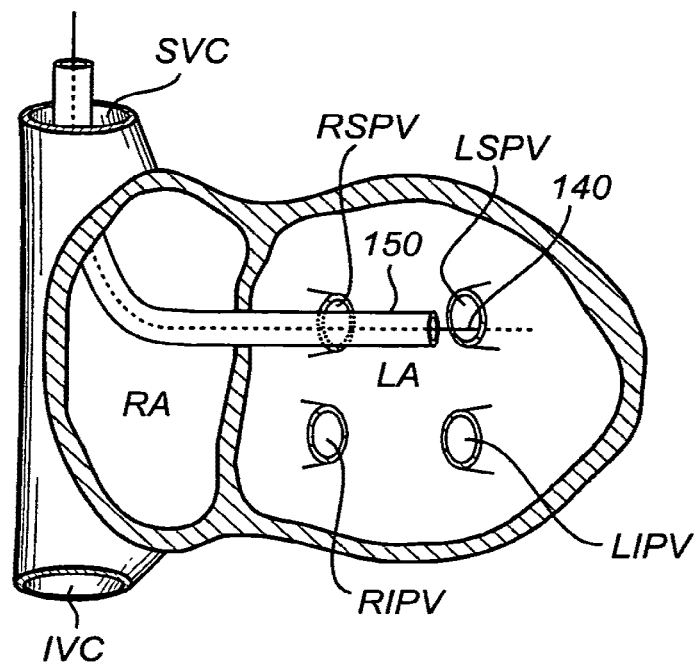
FIGS. 38-40 illustrate the deployment of a tissue lesion creating device in the left superior pulmonary vein.
Figure 39:
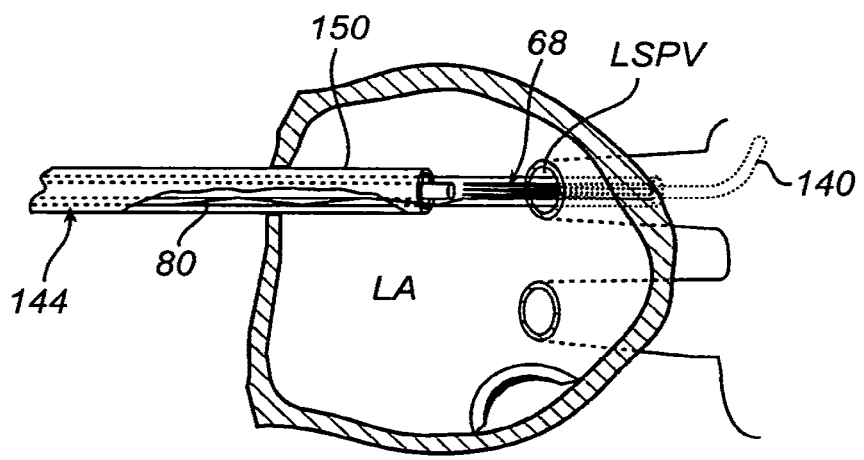
Figure 40:
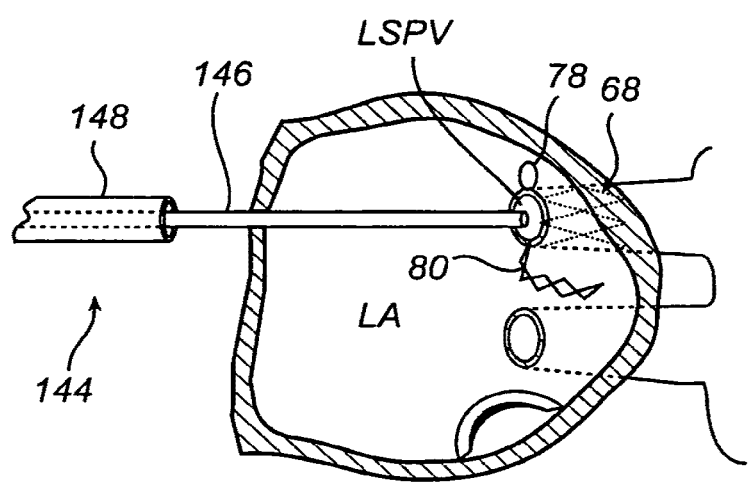

Thereafter, the guide wire 140 is again retracted into the LA and inserted into the LSPV, as illustrated in FIG. 38. Then, the fourth cutting device 68 is inserted using a guide catheter 150 extending to the LSPV orifice and a delivery catheter 144, as illustrated in FIG. 39, in a manner similar to the insertion of the second and third cutting devices 38, 54. Thus, the orientation of the cutting arm 80 of the fourth cutting device 68 is determined in the same manner as for the second and third cutting devices 38, 54. The fourth cutting device 68 may have two cutting arms, which are adapted to extend towards the second cutting device 38 and towards the LAA. Having correctly positioned the fourth cutting device 68, the tubular part 70, the atrial end 78 and the one or two cutting arms 80 of the fourth cutting device 68 are released in a manner similar to the release of the second and third cutting devices 38, 54, as further illustrated in FIG. 40. Now, the cutting arms are released and allowed to assume their radial extension from the tubular part 70, whereby they will penetrate the heart wall to contact the second cutting device 38 or extend to the orifice of the LAA, respectively.

Again, the guide wire 140 is retracted into the LA and inserted into the RSPV. Then, the fifth cutting device 82 is inserted using a guide catheter 150 extending to the RSPV orifice and a delivery catheter 144 in a manner similar to the insertion of the second, third and fourth cutting devices 38, 54, 68. Usually, the fifth cutting device 82 has no cutting arm and therefore only the axial position of the fifth cutting device 82 needs to be determined. Having correctly positioned the fifth cutting device 82, the tubular part 84, and the atrial end 92 of the fifth cutting device 82 are released in a manner similar to the release of the second, third, and fourth cutting devices 38, 54, 68.

Once again, the guide wire 140 is retracted into the LA and now inserted into the LAA. Then, the sixth cutting device 94 is inserted using a guide catheter 150 extending to the LAA orifice and a delivery catheter 144 in a manner similar to the insertion of the other cutting devices. The sixth cutting device 94 is advanced into a position where the entire sixth cutting device 94 is inside the LAA, and a proximal end of the sixth cutting device 94 is adjacent to the LAA orifice. The delivery catheter 144 has a marker on the catheter outside the patient, as well as a x-ray marker 149 visible on the fluoroscopy, indicating securely the orientation of the sixth cutting device 94 such that the elliptic shape of the sixth cutting device 94 may be oriented in correspondence to the elliptic shape of the LAA. When the correct position of the sixth cutting device 94 is confirmed by means of fluoroscopy, a distal end of the sixth cutting device 94 is released from the delivery system far inside the LAA, whereby the distal end will expand radially towards the wall of the LAA to fix the position of the sixth cutting device 94. Next, a mid portion of the sixth cutting device 94 and a proximal end are released. Now, the sixth cutting device 94 is allowed to change its shape to cut through the heart wall of the LAA.

Now, the guide wire 140 is retracted from the LA into the RA and inserted into the RAA. Then, another sixth cutting device 94 is inserted using a guide catheter 150 extending to the RAA orifice and a delivery catheter 144 in a manner similar to the insertion of the other cutting devices. The other sixth cutting device 94 is advanced into a position where the entire sixth cutting device 94 is inside the RAA, and a proximal end of the sixth cutting device 94 is adjacent to the RAA orifice. The position of the sixth cutting device 94 is determined in a manner similar to the positioning of the sixth cutting device 94 inserted into the LAA. When the correct position of the sixth cutting device 94 is confirmed, the sixth cutting device 94 inserted into the RAA is released in a manner similar to the release of the sixth cutting device 94 inserted into the LAA. Now, the sixth cutting device 94 is allowed to change its shape to cut through the heart wall of the RAA.

Figure 41:
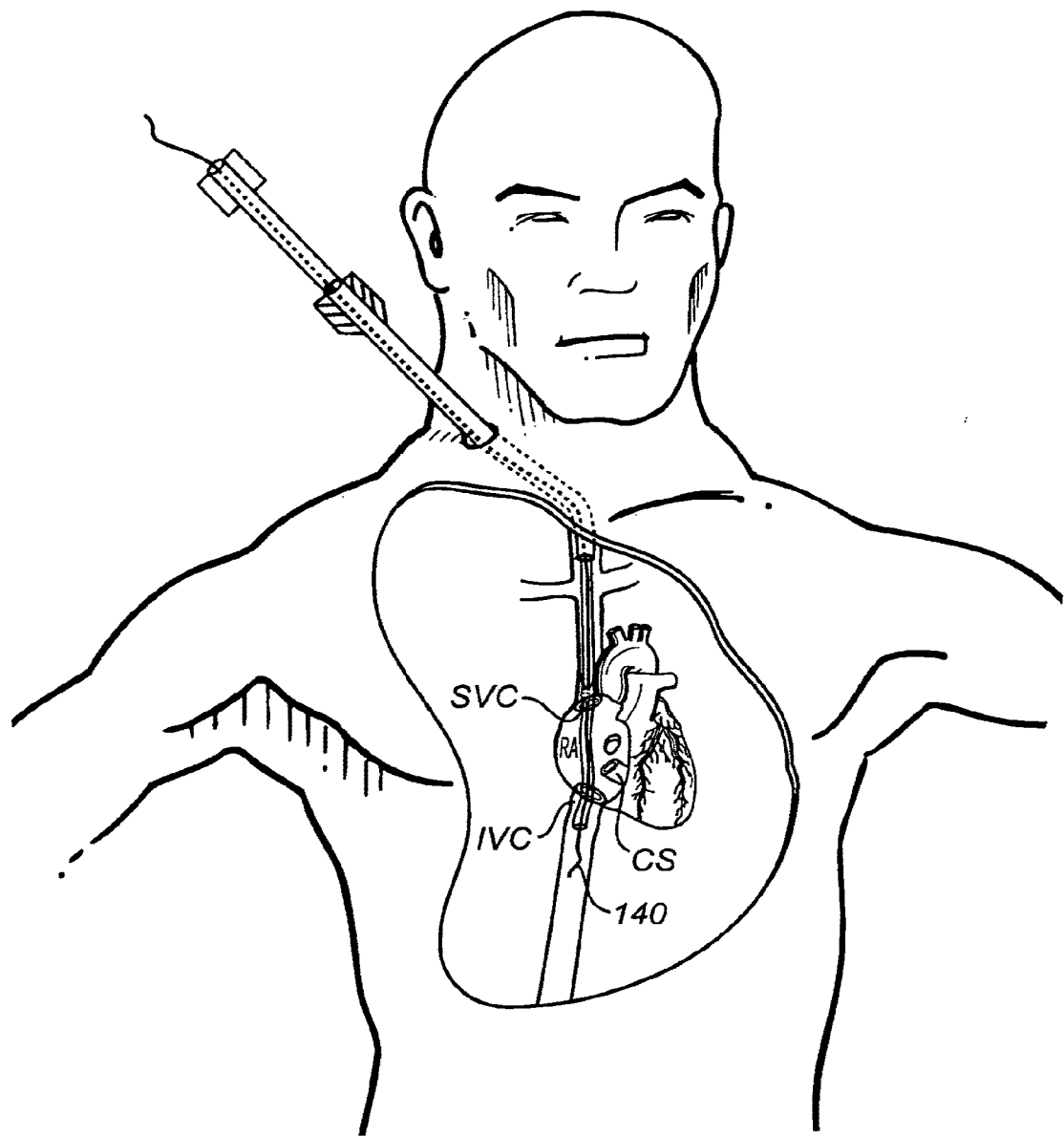
FIGS. 41-44 illustrate the insertion of a tissue lesion creating device into the inferior and superior vena cava.
Figure 42:
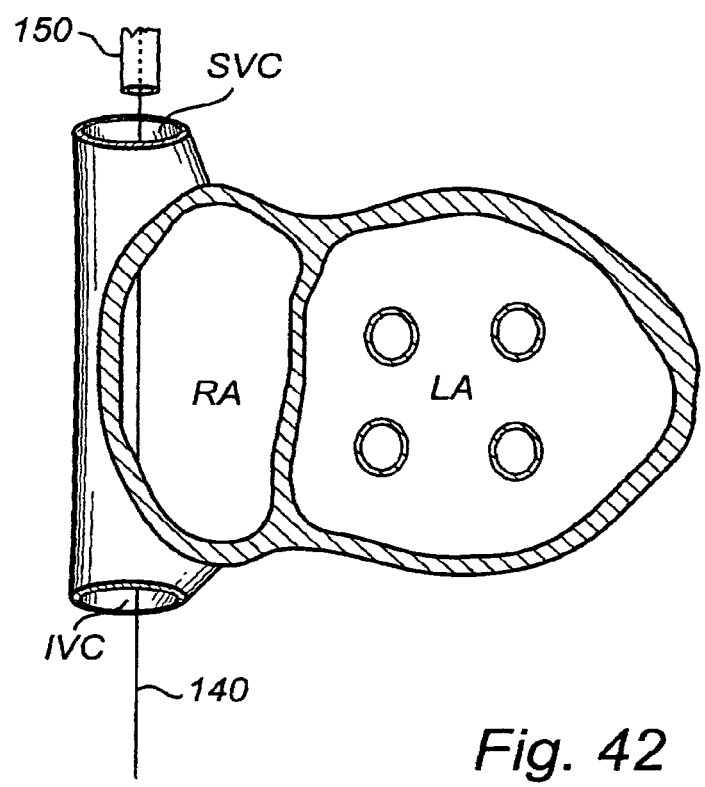
Figure 43:
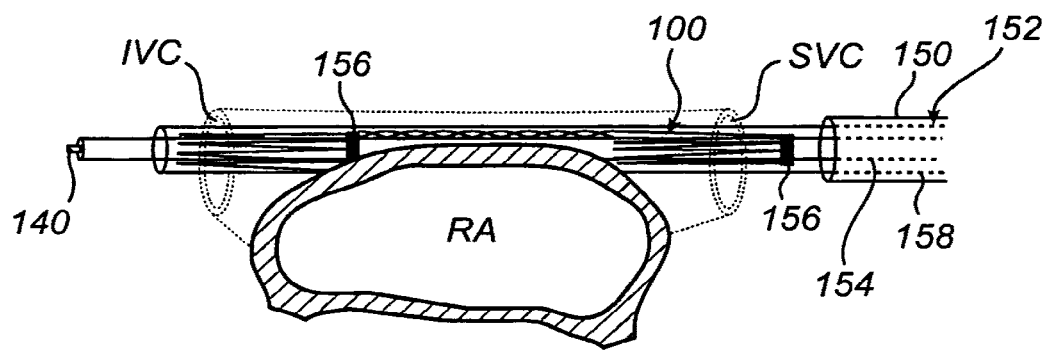
Figure 44:
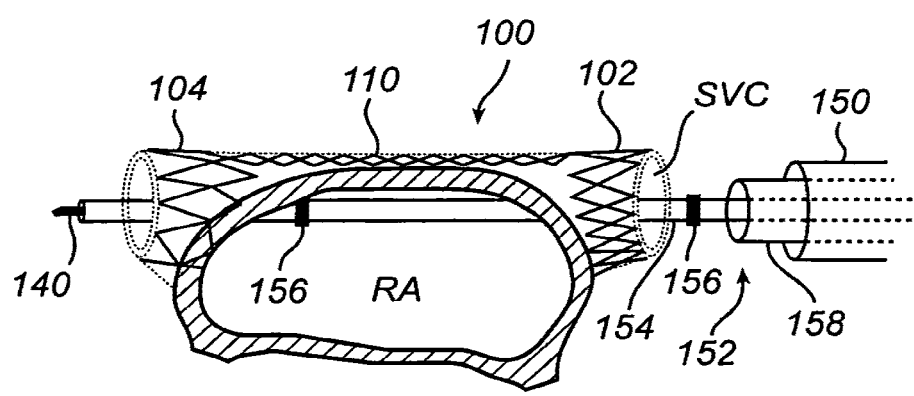

Next, the guide wire 140 is retracted from the RAA into the RA. If the access point to the vascular system was created in the upper part of the body, the guide wire 140 extends through the SVC into the RA. Then, the guide wire 140 is further inserted into the IVC, as illustrated in FIG. 41. On the other hand, if the access point to the vascular system was created in the lower part of the body, the guide wire 140 extends through the IVC into the RA. Then, the guide wire 140 is further inserted into the SVC. Thereafter, the seventh cutting device 100 is inserted using a guide catheter 150, as illustrated in FIG. 42, and a delivery catheter 144 in a manner similar to the insertion of the other cutting devices. The seventh cutting device 100 is placed in position in the IVC, SVC and the RA, as illustrated in FIG. 43. The delivery catheter 152 carries the seventh cutting device 100 on the inner part 154 of the catheter 152. The inner part 154 comprises stops 156, which prevent the seventh cutting device 100 from being axially displaced from the inner part 154 during insertion of the device. Again, the cutting device 100 is kept in a contracted, temporary state by means of a restraining part 158. The correct orientation of the seventh cutting device 100 is obtained in a manner similar to the positioning of the second, third and fourth cutting devices 38, 54, 68. The seventh cutting device 100 has now been rotated into a position where it will change shape in such a way that its cutting arm or cutting arms 122 will extend in intended directions. Thus, the seventh cutting device 100 may comprise a cutting arm 122 that extends towards the orifice of the CS and/or a branch 112 that extends from the connecting cutting arm 110 of the seventh cutting device 100 towards the lateral wall of the RA. When the correct position of the seventh cutting device 100 is confirmed by means of fluoroscopy, a distal end of the seventh cutting device 100 in the delivery catheter 152 is released from the delivery catheter 152 in the IVC or SVC, depending on where the distal end of the delivery catheter is placed. Thereafter, the connecting cutting arm 110 is released and finally a proximal end of the seventh cutting device 100 is released, as illustrated in FIG. 44.

Now, the guide wire 140 and the delivery catheter 152 is retracted outside the patient, since all parts of the treatment kit have been implanted.

On special indication, for instance when it is difficult to place the guide wire inside the PVs, an arterial access may be used instead. The insertion technique is identical, except that the access to the vascular system is achieved by puncture of an artery and that the cutting devices are delivered through the arterial system instead of through the venous system. After puncture of the artery, a catheter is advanced through the aorta and passed by the aortic valve into the left ventricle and finally into the LA. The guide wire is advanced into the desired PV and the insertion of the cutting device may then be achieved in the manner described above.

The cutting devices have now been released such that they may change their shapes to obtain their permanent shapes. During the change of shape, each cutting device will penetrate heart tissue in the path of the change of shape. Thus, the cutting devices will now create the cutting pattern intended for forming blocks against propagation of undesired electrical signals in the heart. After the cutting devices have made their change of shape, the needed effect of the cutting devices on the heart tissue is completed. Thus, if the cutting devices are made of resorbable shape memory polymers, the cutting devices will be resorbed a time after termination of the cutting procedure. This time for resorption can be set by determination of the different ingredients of polymers and also by means of external altering, for instance by means of x-ray radiation, ultrasound, electron beams, or light of a defined wavelength, setting the time of the polymers to be resorbed. However, the cutting devices may also be left in the body after the change of shape, or only some of the cutting devices may be resorbed.

It should be emphasized that the preferred embodiments described herein is in no way limiting and that many alternative embodiments are possible within the scope of protection defined by the appended claims.

What is claimed is:

1. A kit of shape-changing devices for treatment of disorders in a heart rhythm regulation system, said kit comprising:
   shape-changing devices, which each has a first and a second state, wherein the device in the first state has such dimensions as to be insertable to a desired position within the vascular system, and wherein the device is capable of changing shape to the second state when located at said desired position, the device in the second state having a tubular part, which strives to a diameter that is larger than the diameter of the vessel at the desired position, whereby the tubular part has expansion characteristics so as to circumferentially cut through an entire vessel wall of said vessel along an entire circumference and along a length of the tubular part into a tissue surrounding the vessel at the desired position and destroy the tissue in order to prevent the tissue from transmitting electrical signals,
   wherein at least one of the shape-changing devices is adapted to be inserted to a position at an orifice of a pulmonary vein in a heart, and at least one of the shape-changing devices is adapted to be inserted to a position in a coronary sinus.

2. The kit as claimed in claim 1, wherein the shape-changing device that is adapted to be inserted to a position at the orifice of the pulmonary vein comprises an arm, which in the second state is arranged to contact the shape-changing device adapted to be inserted to the position in the coronary sinus.

3. The kit as claimed in claim 2, wherein said arm comprises a trough in an area to come in contact with the shape-changing device adapted to be inserted to the position in the coronary sinus.

4. The kit as claimed in claim 1, wherein at least one of the shape-changing devices is adapted to be inserted into an inferior vena cava.

5. The kit as claimed in claim 4, wherein at least one of the shape-changing devices is adapted to be inserted into a superior vena cava.

6. The kit as claimed in claim 5, wherein at least one of the shape-changing device that is adapted to be inserted into the superior vena cava and the shape-changing device that is adapted to be inserted into the inferior vena cava comprises an arm, which in the second state is arranged to form a connection between these shape-changing devices.

7. The kit as claimed in claim 1, wherein the kit comprises four shape-changing devices, each being adapted to be inserted into a respective pulmonary vein.

8. The kit as claimed in claim 7, wherein at least a first of the four shape-changing devices adapted to be inserted into a respective pulmonary vein comprises an arm, which in the second state is arranged to contact at least a second of the four shape-changing devices adapted to be inserted into a respective pulmonary vein.

9. The kit as claimed in claim 1, wherein at least one of the shape-changing devices is adapted to be inserted into a left atrial appendage.

10. The kit as claimed in claim 9, wherein the shape-changing device that is adapted to be inserted into the left atrial appendage comprises an arm, which in the second state is arranged to contact the shape-changing device adapted to be inserted to the position at the orifice of the pulmonary vein.

11. The kit as claimed in claim 9, wherein the shape-changing device that is adapted to be inserted into the left atrial appendage comprises a film, which covers an end of the tubular shape of the device in the second state.

12. The kit as claimed in claim 1, wherein at least one of the shape-changing devices is adapted to be inserted into a right atrial appendage.

13. A kit for heart rhythm treatment comprising:
   a plurality of heart rhythm treatment devices having a compressed configuration that is sized for advancing within a vascular system of a patient and an expanded configuration forming a tubular shape with a diameter larger than a diameter of a desired target location within a body such that said tubular shape circumferentially cuts entirely through a tissue of said target location along an entire circumference and along a length of the tubular shape;
   wherein a first heart rhythm treatment device of said plurality of heart rhythm treatment devices is sized and curved to fit within a coronary sinus.

14. The kit of claim 13, wherein a second heart rhythm treatment device is shaped to fit within a left inferior pulmonary vein.

15. The kit of claim 14, wherein a third heart rhythm treatment device is shaped to fit within a right inferior pulmonary vein.

16. The kit of claim 15, wherein a fourth heart rhythm treatment device is shaped to fit within a left superior pulmonary vein.

17. The kit of claim 16, wherein a fifth heart rhythm treatment device is shaped to fit within a right superior pulmonary vein.

18. The kit of claim 17, wherein a sixth heart rhythm treatment device is shaped to fit within a left or right atrial appendage.

19. The kit of claim 18, wherein a seventh heart rhythm treatment device is shaped to fit within an inferior or a superior vena cava.

20. A kit of shape-changing devices for treatment of disorders in a heart rhythm regulation system, said kit comprising:

a first device having a compressed state for delivery within a vascular system and an expanded state sized for circumferentially cutting entirely through a left inferior pulmonary vein along an entire circumference of the left inferior pulmonary vein and pressing into a heart atrium;

a second device having a compressed state for delivery within the vascular system and an expanded state sized for circumferentially cutting entirely through a right inferior pulmonary vein along an entire circumference of the right inferior pulmonary vein and pressing into said heart atrium;

a third device having a compressed state for delivery within the vascular system and an expanded state sized for circumferentially cutting entirely through a left superior pulmonary vein along an entire circumference of the left superior pulmonary vein and pressing into said heart atrium;

a fourth device having a compressed state for delivery within the vascular system and an expanded state sized for circumferentially cutting entirely through a right superior pulmonary vein along an entire circumference of the right superior pulmonary vein and pressing into said heart atrium; and a fifth device having a compressed state for delivery within the vascular system and an expanded state sized for circumferentially cutting entirely through a coronary vein along an entire circumference of the coronary vein; said expanded state being further curved to conform to said coronary vein.

* * * * *